US005936078A

United States Patent [19]

Kuga et al.

[11] Patent Number: 5,936,078
[45] Date of Patent: Aug. 10, 1999

[54] DNA AND PROTEIN FOR THE DIAGNOSIS AND TREATMENT OF ALZHEIMER'S DISEASE

[75] Inventors: Tetsuro Kuga; Satoshi Nakagawa, both of Machida; Yoshiyuki Sakaki, Tokyo; Nanding Zhao, Tokyo; Hideji Hashida, Tokyo, all of Japan

[73] Assignee: Kyowa Hakko Kogyo Co., Ltd., Tokyo, Japan

[21] Appl. No.: 08/909,965

[22] Filed: Aug. 12, 1997

Related U.S. Application Data

[63] Continuation of application No. PCT/JP96/03630, Dec. 12, 1996.

[30] Foreign Application Priority Data

Dec. 12, 1995 [JP] Japan ...................................... 7-322745

[51] Int. Cl.⁶ .......................... C07H 21/04; C12N 15/12
[52] U.S. Cl. ...................................... 536/23.5; 536/24.31
[58] Field of Search .............................. 514/44; 536/23.1, 536/23.5, 24.3, 24.31, 24.33, 24.5

[56] References Cited

FOREIGN PATENT DOCUMENTS

93/00353  1/1993  WIPO .
94/23756  10/1994  WIPO .

OTHER PUBLICATIONS

Molecular Brain Res. (1992), vol. 14, pp. 109–116 Walker et al.
Mol. Cel. Neurosciences (1992), vol. 3, pp. 461–470 Alberts et al.
Genomics (1996), vol. 36, No. 1, pp. 86–99 Couch et al.
Hum. Mol. Genet. (1993), vol. 2, No. 11, pp. 1793–1798 Takeda et al.
Genomics (1994), vol. 23, No. 2, pp. 379–389 Murakawa et al.
Nat. Genetics (1993), vol. 4, No. 4, pp. 373–380 Adams et al.
Proc. Natl. Acad. Sci. USA (1992), vol. 89, No. 14, pp. 6333–6337.
Genomics (1996), vol. 34, No. 2, pp. 198–204 Palmiter et al.
Verma et al. (1997) Gene therapy–promises, problems and prospects. Nature 389:239–242, Sep. 1997.
Diedrich et al. (1991) Neuropathological changes in scrapie and Alzheimer's disease are associated with increased expression of apolipoprotein E and cathepsin D in astrocytes. J. Virol. 65:4759–4768, Sep. 1991.
de la Monte et al. (1990) Enhanced expression of an exocrine pancreatic protein in Alzheimer's disease and the developing human brain. J. Clin. Invest. 86:1004–1013, Sep. 1990.
Duguid et al. (1989) Changes in brain gene expression shared by scrapie and Alzheimer disease. Proc. Natl. Acad. Sci. USA 86:7260–7264, Sep. 1989.
Tsuji et al. (1992) Molecular cloning of human growth inhibitory factor cDNA and its down–regulation in Alzheimer's disease. EMBO J. 11:4843–48–50, Dec. 1992.
Strada et al. (1992) Decreased choline acetyltransferase mRNA expression in the nucleus basalis of Meynert in Alzheimer's disease: and in situ hybridization study. Proc. Natl. Acad. Sci. USA 89:9549–9553, Oct. 1992.
Lacopino et al. (1990) Specific reduction of calcium–binding protein (28–kilodalton calbindin–D) gene expression in aging and neurodegenerative diseases. Proc. Natl. Acad. Sci. USA 87:4078–4082, Jun. 1990.
Andersson et al. (Mar. 30, 1997) Human clone 23652 mRNA sequence. Genbank. Accession No. U913891. Accessed Mar. 13, 1998.
Hunt (Jul. 11, 1996) Human DNA sequence from cosmid 130N4. Genbank. Accession No. Z75888. Accessed Mar. 13, 1998.

Primary Examiner—George C. Elliott
Assistant Examiner—Robert Schwartzman
Attorney, Agent, or Firm—Fitzpatrick, Cella, Harper & Scinto

[57] ABSTRACT

The present invention relates to a DNA selected from DNAs, each having the nucleotide sequence of one of Sequence Nos. 1 to 17, complementary to the RNA strand of mRNA with the varied expression level in patients with Alzheimer's disease, compared with the expression level of the mRNA in normal human brain or a DNA hybridizable with the above-mentioned DNA wherein one or more nucleotides in said DNA are deleted or substituted with other nucleotides or one or more nucleotides are added to said DNA, a polypeptide encoded by the DNA, an antibody recognizing the polypeptide, and the diagnosis, therapeutic treatment and research works of patients with Alzheimer's disease, using the DNA, the polypeptide and the antibody.

3 Claims, No Drawings

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 2688 base pairs
      (B) TYPE: nucleic acid
      (C) STRANDEDNESS: double
      (D) TOPOLOGY: linear (ii) MOLECULE TYPE: cDNA to mRNA (vi) ORIGINAL SOURCE:
      (A) ORGANISM: human (vii) IMMEDIATE SOURCE:
      (B) CLONE:F55

(ix) FEATURE:
      (A) NAME/KEY: CDS
      (B) LOCATION: 358 to 486
      (B) LOCATION: 560 to 799
      (B) LOCATION: 1042 to 1182
      (B) LOCATION: 2105 to 2269
      (B) LOCATION: 2370 to 2462
      (C) IDENTIFICATION METHOD: by experiment (xi) SEQUENCE DESCRIPTION: SEQ ID NO:1:

```
GAATTCGGCA CGAGAATGAG CCCCACAGAA TAAAGGTTTT TCCTCTTGCT GTGGCCTACT    60

GGAAGCCTTC CTAACTCTAT AGCTGGTAAA GTAGAGCAGA AAGGGCCAGA ATGGCTTAAG   120

ATGGAGCTAA ATCCCTATAG CATTCCATTT TCTGCTCTTG CCTCTTGAAC TTAGAAGGCT   180

TGCCCATATA TCCTAACAAT CTGTTCTCTG AGCTGTTAGG CCAATCCCTG GTCTCAAACT   240
```

```
CCTGACCTCA GGTGATCCAC CCACTATGGC CTCCCAAGGT GCTGGGATTG CAGATGTGAG    300

CCACCGTGCC TGGCCAGAAA ATCTGGATTC TTATTCCTAG TTCTTCATTT CTGTCAC AT    359
                                                            Met
                                                             1

G CAC TTA GTT GAC ATT ACA TCT ACA TAT ATT AGC TTT TTC CTA CAT GAG    408
  His Leu Val Asp Ile Thr Ser Thr Tyr Ile Ser Phe Phe Leu His Glu
          5                  10                 15

CCA TCT ATT TAC TTA GTA ACC AGT GTT CTT AAT GAA GTA TTT AGT CTT      456
Pro Ser Ile Tyr Leu Val Thr Ser Val Leu Asn Glu Val Phe Ser Leu
         20                  25                 30

GGG TTT CTT GTA AAA TTT CTC TGC ATT CCT TAGACAGTGT ACTATACATG        506
Gly Phe Leu Val Lys Phe Leu Cys Ile Pro
         35                  40

AAATATTCTT GTTGACCTAG TAATTTATAT TATTCCATTT AATTCTTAAA CCT ATG       562
                                                          Met
                                                           1

GCC TTT TTA TTG AGC ACA CTC TTA AAT CAT TAT TTG GCT TGT AAA CAT      610
Ala Phe Leu Leu Ser Thr Leu Leu Asn His Tyr Leu Ala Cys Lys His
             5                  10                 15

TCA TCT GAA TTG TGG CTA CAA TCC TCT TTA AAT AAT CTA GGA AAA AAG      658
Ser Ser Glu Leu Trp Leu Gln Ser Ser Leu Asn Asn Leu Gly Lys Lys
         20                  25                 30

AAA GAT AAA GCT TAC ATT TTC ACA GTT TTG GCT CTT AAA CAC ATT CCA      706
Lys Asp Lys Ala Tyr Ile Phe Thr Val Leu Ala Leu Lys His Ile Pro
         35                  40                 45

CAA ATG CCA TTA AGA ATT TAT TTT GTT TTA GGC CAG TCA TGG TGG CTC      754
Gln Met Pro Leu Arg Ile Tyr Phe Val Leu Gly Gln Ser Trp Trp Leu
 50          55                  60                         65

ATG CCT GTA ATC CCA GCA ATT TGG GAG GCT GAG GCA AGA ACT GCT          799
Met Pro Val Ile Pro Ala Ile Trp Glu Ala Glu Ala Arg Thr Ala
                 70                  75                 80

TGAGCCCAGG AGTTTGAGAC TAGCCTGGGC AACATAGCAA GACCCTGTCT CTACCAAAAA    859

AAAAAAAGTT TATTTTGTTT TAGAGTCATT TAATGTGTTT TTATGCACAA TAATAGTGGG    919

AGGTTGTTTT GTTGCATTTG TTTGTTTGTT TTGTTTTGTT TTGTTTTGCT TTCCATGTGG    979

GAAAAGTTAA CATTGGAACT GTTTCTAGTA AAAGATTTTT TTCAGGCTGG GCACGGTGGC   1039

TC ATG CCT GTG ATC CCA ACA CTT TGG GAG ACC GAG GGA GCT GGA TCA      1086
   Met Pro Val Ile Pro Thr Leu Trp Glu Thr Glu Gly Ala Gly Ser
    1           5                  10                 15

CCT GAG GTC AGG AGT TCG AGA CCA GCC TGG CCA ACA TGG AAA AAC TCC     1134
Pro Glu Val Arg Ser Ser Arg Pro Ala Trp Pro Thr Trp Lys Asn Ser
             20                  25                 30

ATC TCC ACT AGA AAT ACA AAA GTA GCC TGG TGT GGT GGC ACA TGC CTG     1182
Ile Ser Thr Arg Asn Thr Lys Val Ala Trp Cys Gly Gly Thr Cys Leu
         35                  40                 45

TAATCCCAGC TACTTGGGAA GCTGAGGCAG GAGAATCACT TGAACCTGGG AGGTGGAGGT   1242

TGCAGTGAGC CAAGATCACG CCATTGCACT CCAGCCTGGG CAACAAGAGT GAAACTCCGT   1302

CTCAAAAAAA AAAAAAAAAA AGATGTTTTT CATTTTTTTC ATGTTATCTA TCCAAGCACT   1362

GTTCCATGGT CAGCAAGTCA TATTTCATAA TGTGGATTTT CCAAAATAAT TATTGAATAC   1422

AGCTATTCTA TGGCTACTTT TAGTGTTTTT GTGGTATGTG GTGTGGGAGT GTTTATGAA    1482

TTACCAGTAT CTTAAATTTT CAAAGGAACC TTGGAAGTCT ATCACTCTAA ATGAAAGTCT   1542

GTCACTCTAC ATGAATTATG TGCTCAAATT TGACCAACTC AGTTTAAGAC ACAAAACAGT   1602

AATTTGAAGA AGGAAAAATG AAGAGAGTTT CTAGTTTAAT GGGTAAATTT TTTGTTGTTG   1662

CAATAGTAAG TTTAGTCTTC TTATAATATT TCTAAATGAA AAATCATAGG TATTTGTTAC   1722
```

```
CATGTGTGAA GATTACTTTG TTAAAAGCAA AAGTGGTCGT GTGATATGCT AAATGTTAAT    1782

TACTGATTTT ATATGTTTAA ATCACGCCAA ACAAATTATG TCTGTGCCAT CCAGGGTCTG    1842

TTGTTAATCT TTTTCTGAGT ACTTGGATTG GGATAAAGGG CTTGTACTAT GCACTTTTA    1902

TTAATGAATA AATAGAAAAC GTTAGTAACA CTTTGTGTTT TCTGTTTGGC TTTTGTGGGA    1962

AGAGAAGCAA GCATCTTTTG CCTAGTAGAT GTTAACATTG TGTATTAAAC AGTTTCTTTG    2022

TAAGACCTAA CTAAAGACAT TCCTAAGAGA GAACTTAAGT TTTAAGAAAA GTTGTGAGAA    2082

AAATATTCAT AAAATATGCA GT ATG GGG CCA GTA TTC AGA AGT AGA GTT TCT    2134
                        Met Gly Pro Val Phe Arg Ser Arg Val Ser
                         1               5                  10

CTC TTG GAA ATT AGA TTG CAG TCA CAT TTC TTT GGT TAT TTT CTT TCT    2182
Leu Leu Glu Ile Arg Leu Gln Ser His Phe Phe Gly Tyr Phe Leu Ser
             15              20                  25

CTC TCT CTT CCT AGA ATA CCA GGT AAA ATA GAC ATT TAC TTT GAG GGA    2230
Leu Ser Leu Pro Arg Ile Pro Gly Lys Ile Asp Ile Tyr Phe Glu Gly
         30              35                  40

CTA ATA TCC AAT AGT GTT AAT TAT TTA AGC AGA TAT ATC TAGCTCAAAA    2279
Leu Ile Ser Asn Ser Val Asn Tyr Leu Ser Arg Tyr Ile
     45              50                  55

GGAACCAGAC ATGTCACTGT ACCAAAAACA CACAAAAGTG AAAATTTGCT TCTGTTCTGT    2339

GACCTAGAAT GTGTCCAGAC ATTAAAGATC ATG AAT ACT CAT ATA CAT GTA AAA    2393
                                 Met Asn Thr His Ile His Val Lys
                                  1               5

ATA GTA ACA CTG CTC TGG CAT GAT TTT GAC GTC AGT GTT TAT GTA ATA    2441
Ile Val Thr Leu Leu Trp His Asp Phe Asp Val Ser Val Tyr Val Ile
     10              15                  20

ACT TCA GTG TTA TAT TTA AAA TAGATAAATT TGTGAAATAA CAATTTCTTG    2492
Thr Ser Val Leu Tyr Leu Lys
     25              30

GAGACAGTCA ACTTTTTATG ATTTAATCTA AAGATTGTCA TGTACATGTC AACGGATATC    2552

TGAATCCTCA GTGAAACTGT TAAGTTTTCA TTAAATGACT CTGCTGCAAT ACTAGTTTTC    2612

TTCTCAGAAA ATGGAATTCA AATAAAATAA GTTTTTTGGT CTTGGAAAAA AAAAAAAAA    2672

AAAAAAAAAA AAAAA    2688

(2) INFORMATION FOR SEQ ID NO:2:

(i) SEQUENCE CHARACTERISTICS:
        (A) LENGTH: 1016 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (B) CLONE:F99

(ix) FEATURE:
        (A) NAME/KEY: CDS
        (B) LOCATION: 231 to 320
        (B) LOCATION: 382 to 483
        (B) LOCATION: 641 to 832
        (C) IDENTIFICATION METHOD: by experiment (xi) SEQUENCE DESCRIPTION: SEQ ID NO:2:

GAATTCGGCA CGAGAAGAAA CTTAGCCAGG CACTGAGTGC GTGGGAAGGC AAAACACTCT    60

TTTCTCCTCC CACGGCGGGG GCGCTCCCTG GGCGATGCTC ACGGAGAGTG GGAGGGCGTC    120
```

-continued

```
CCGCACCGGG CAGAGCTGAA GGGTGGCGGG GGTCGGCTTC CTCCTCTCTG CCTCTTCCCT    180

TCCGCCACGC TTCCTACCCA CACCAGCCAG TCTCCAGTAA CAGATATAGA ATG CCT        236
                                                      Met Pro
                                                        1

TCA TTT GGA ACA CGG AGA GAC AAG CGT GCC GTG TGG GAA GGA GAG AAG      284
Ser Phe Gly Thr Arg Arg Asp Lys Arg Ala Val Trp Glu Gly Glu Lys
          5                  10                  15

CCG CTG CTG GAG CAA GCG TGG TCC CAG AGG AGA GCC TGATTTGAGT           330
Pro Leu Leu Glu Gln Ala Trp Ser Gln Arg Arg Ala
 20                  25                  30

TAAAGCGAGA GGGCAGGAGA AGCAGTTGGG AATCGAGGCA GTGGGCCGAG G ATG GCC     387
                                                        Met Ala
                                                          1

CAG GTT CAA GAG GCA CAG TGG GAG GCT GCA GGT GTA AGG AGA AGG ACG     435
Gln Val Gln Glu Ala Gln Trp Glu Ala Ala Gly Val Arg Arg Arg Thr
          5                  10                  15

GCT CAG GTG AGG GCT GCA CAG GCG CTG AGG GGA TGG GGC TCT GGG TGG     483
Ala Gln Val Arg Ala Ala Gln Ala Leu Arg Gly Trp Gly Ser Gly Trp
 20                  25                  30

TGACATCTCC AAGGCAAGAG AGCACGTAGA TTTCAGAGCA AAACTATCTG GGTCAGAATC   543

CCGGATCCAC CCTTTATCAC TATAAAATGT TGGGCAAGTA CTCACAGTGC CTCTGCTCTC   603

TCATGTATAA AATGTGAGGA ACCATAGCAC CAAAATC ATG GAG GTG TTA GGC AGA    658
                                         Met Glu Val Leu Gly Arg
                                           1               5

TGG ATG TGC TGG GAG GAA ACC TGT TTA CTA GGG GGC TGG GTT GGA GAT     706
Trp Met Cys Trp Glu Glu Thr Cys Leu Leu Gly Gly Trp Val Gly Asp
         10                  15                  20

GGG GAG CTT CTT ATG ATG TCT GCT GTC AGC AGC TTT AAA GGA GAT GTG     754
Gly Glu Leu Leu Met Met Ser Ala Val Ser Ser Phe Lys Gly Asp Val
 25                  30                  35

GGT GTC TAT CCT GGT GGT CTC CCT ATC AGC CTG GGA TCA GGT GGT GAG     802
Gly Val Tyr Pro Gly Gly Leu Pro Ile Ser Leu Gly Ser Gly Gly Glu
 40                  45                  50

TGG CTT CAC CTA CTA AGC CCA AAG ATG TGT TAGGAAAACA GGCCGATATC       852
Trp Leu His Leu Leu Ser Pro Lys Met Cys
 55                  60

TATCGATAAG GAAAACTGGC CGGCACGATG GCTCATGCCT GTAATCCCAG CACTTTGGGA   912

GACCAAGGCG GGCCGATCAC CTGAGGTCAG GAGTTCGAGA CCAGCCTGGC CAACATGGCA   972

AAACCCTGTC TCCTAAAA ATACAAAAAA AAAAAAAAAA AAAA                     1016
```

(2) INFORMATION FOR SEQ ID NO:3:

(i) SEQUENCE CHARACTERISTICS:
        (A) LENGTH: 1420 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (B) CLONE:F198

(ix) FEATURE:
        (A) NAME/KEY: CDS
        (B) LOCATION: 378 to 575
        (B) LOCATION: 590 to 709
        (B) LOCATION: 1105 to 1206
        (C) IDENTIFICATION METHOD: by experiment (xi) SEQUENCE DESCRIPTION: SEQ ID NO:3:

```
GAATTCGGCA CGAGCTGGAG AGAAAGCTTA TAAATGTGAA GAATGTCACA AAGTTTACAG    60

TCGCACATCA AACCGTGAAA GACAGGAGAA TTCACACTGG AGAGAAACCA TAAAAATGTA   120

AGAGTTTGTG ACAAGGCTTT TGGGCATGAT TCGCACCTGG CACAACATGC TAGAATTCAC   180

ACTGGAGAGA AACCTTACCA GTGTAATGGG TGTGGCAAAG CCTTTAGTAG GCAGTCAACA   240

CTTGTTTACC GTCAGGCAAT CCATGGTGTA GGGAAACTTT ACTAAGGTAA TGATTGTCAC   300

AAAGTCTTCA GTAATGCTAC AACCATTGTG AATCACTGGA GAATCCATAA GGAAGAGAGA   360

TCATACTAGG GTAATAA ATG TGG CAG ATT TTT CAG ACA TTG TTC ATA CCT     410
                   Met Trp Gln Ile Phe Gln Thr Leu Phe Ile Pro
                    1               5                      10

TGC AGT TCA TCG GTG AAC TCA ACG CTG GAG AGA AAC CTT ACA AAT GTC    458
Cys Ser Ser Ser Val Asn Ser Thr Leu Glu Arg Asn Leu Thr Asn Val
            15                  20                  25

ATG ACT GTG GCA AGG TCT TCA GTC AAG CTT CAT CCT ATG CAA AAC ATA    506
Met Thr Val Ala Arg Ser Ser Val Lys Leu His Pro Met Gln Asn Ile
        30                  35                  40

GGA GAA TTC ATA CAG GAG AGA AAC CTC ACA TGT GTG ATG ATA GTG GCA    554
Gly Glu Phe Ile Gln Glu Arg Asn Leu Thr Cys Val Met Ile Val Ala
    45                  50                  55

AAG CCT TCA CTT CAC ACC TCA TGAGACATCA GAGA ATG CAT ACT GGA CAG    604
Lys Pro Ser Leu His Thr Ser              Met His Thr Gly Gln
60              65                        1                 5

AAA TCT TAC AAA TGT CAT CAA TGT GCC AAG GTC TTC AGT CTG AGT TCA    652
Lys Ser Tyr Lys Cys His Gln Cys Ala Lys Val Phe Ser Leu Ser Ser
            10                  15                  20

CTC CTT GCA GAA TAT GAG AAA ATT CAT TTT GGA GGT AGT TGG TCC ATA    700
Leu Leu Ala Glu Tyr Glu Lys Ile His Phe Gly Gly Ser Trp Ser Ile
        25                  30                  35

TGC AAT GAG TAGAGCAAAC CATCAAGCAT TAATTGACAT TAGGGTCAAT            749
Cys Asn Glu
        40

TCAGCATTGA CTTGAGTTTG TATTGACTTA ACATTGAGTT CAAGCATTAA TTGACATTAG   809

TGTTTATGTT AAGAGGATTG GGCCAGGCAC ATCAGCTTAC ACCTGTAATC TGAGCGCTTT   869

GGGAGGCCAA GGTGGGTAGA TCACTTGAGG TCAGGAGTTT GAGATCAGCC TGGCCAACAG   929

ACGTGAGCCA TTTTCCCAGC CTGTTTTTTG TTTCTTTAAA AAAACTGATA GGGATTTTTA   989

TGGATATCAT GTTGAATCTA AATCACATTG GGTTATTATA TAATCATTTC ACAATATTAA  1049

TTTTTCCAAG CTATCAATAT GGGTTGTAGC TCAATGTTTT TAATCATTTT GATCA ATG   1107
                                                             Met
                                                              1

TTT GTA GAT TTC AAG GTA CAA ACT TCT GAC CTT TGT ACG TTT ATT TCT   1155
Phe Val Asp Phe Lys Val Gln Thr Ser Asp Leu Cys Thr Phe Ile Ser
            5                   10                  15

AAG TAT TTC TTT AAG TTC TCC AGC AAA TGG AAG TGT TTT AAA ATT TTC   1203
Lys Tyr Phe Phe Lys Phe Ser Ser Lys Trp Lys Cys Phe Lys Ile Phe
            20                  25                  30

TTT TAAAATTGTT TATTGTTAAA GTATGGAAAT TCAACTAATT TTTGGTGCTG         1256
Phe

ATACTGTATT GTGCAAATCC ACTGACTATG TTACTTAGTT CCAGTAGTAT TTTGGTTGGC  1316

TCTTTGTGAT TTTCTACACA GAAGATTATG TCATCTACAA ACAAATATAA TTTTACTTCT  1376

TAAAAAAAAA AAAAAAAAAA AAAAAAAAAA AAAAAAAAAA AAAA                  1420
```

(2) INFORMATION FOR SEQ ID NO:4:

(i) SEQUENCE CHARACTERISTICS:
    (A) LENGTH: 1278 base pairs
    (B) TYPE: nucleic acid
    (C) STRANDEDNESS: double
    (D) TOPOLOGY: linear (ii) MOLECULE TYPE: cDNA to mRNA (vi) ORIGINAL SOURCE:
    (A) ORGANISM: human (vii) IMMEDIATE SOURCE:
    (B) CLONE:F328

(ix) FEATURE:
    (A) NAME/KEY: CDS
    (B) LOCATION: 166 to 261
    (B) LOCATION: 704 to 829
    (C) IDENTIFICATION METHOD: by experiment (xi) SEQUENCE DESCRIPTION: SEQ ID NO:4:

```
GAATTCGGCA CGAGGACTGC AATTGGAGTA TTTCATGGTA TGGCTTGATA AAATAAGTTT    60

TAACTACCTT ATCCATAATA CACTCTGATC CTCAAATAAG TAAAATTTTA ATCCATGTGT   120

TTTGAAAACC CATGGATTAA ACACACAGAT TAGGAAGGAG TACCT ATG GAA TGT GAA   177
                                                Met Glu Cys Glu
                                                 1

GAC CTG GAA ACG GAT TGC CTA AGA GTT ATC CAA GCA AAA AAA GAA AAA    225
Asp Leu Glu Thr Asp Cys Leu Arg Val Ile Gln Ala Lys Lys Glu Lys
 5              10                  15                  20

AAA AAA AAA AAG AAT TAT CCA AGC ATA TGC ACT CCT TAGAGATTCC         271
Lys Lys Lys Lys Asn Tyr Pro Ser Ile Cys Thr Pro
             25                  30

TCGTGCCCCA AAGTGAAGAC TTCCATACTA TACCATGCCA AAGAGCTCCT GGATAAGTTT   331

TCCTGACTCA TAACACAACT GTTCTTCCTA TTCTTCTGTT TCAAAGAGGA AACAGAGCAT   391

TTTAGTATAT TTGAAAGAAT ACACATCACT AACGCCTGGT GCTTCAGTGT TTCCAAATCA   451

CCATGCTTTC CAACATGGGC TAAAATACAG TAGCCCCCAT TACGTGTGGG GGATATGTTC   511

TAAGACCCCC AGAGGATGCC TGAAACCACA GATAGTATCA AACCCTATAC AGCCCATCTT   571

TTCCTATATG TATGTGCATA GATACCCATG AGGAAGTTTA ATTTATAAGT TGGGCACAGC   631

AAGAGATTAA CATTAATAAC TAATACTAAA ATAGAACAAT TAAAACAATA TATTGTAATA   691

AAAGTTATGT GA ATG TGC TCT CAA AAA TAT CTT TTT TTT GTT TTG AGA CGG   742
              Met Cys Ser Gln Lys Tyr Leu Phe Phe Val Leu Arg Arg
               1                   5                      10

AGT CTC ACT CTC ACT CAG GCT GGA GTG CAG TGG CAC AAT CTC GGC TCA    790
Ser Leu Thr Leu Thr Gln Ala Gly Val Gln Trp His Asn Leu Gly Ser
         15                  20                  25

CCA CAA CCT CTG CCT CCT GGG TGT GGT GGT GGG TGC CTA TAATCCCAGC    839
Pro Gln Pro Leu Pro Pro Gly Cys Gly Gly Gly Cys Leu
 30                  35                  40

CACTCAGGAA GCTGAGGCAA GAGAACTGCT TGAACCTGGG AGGTGGAGGT TGCAGTGAGC   899

CAAGATCGTG CCATTGCACT CCAGCCTGGG CAAATAGAGT GAAACTCCGT CTCAAGAAAT   959

AAAAAAGAAA AGCCCAGGTG CAGTGGCTCA TGCCTGTAAT CCCAGAACTT TGGGAGGCCA  1019

AGGCGGGTGT ATCACTTGCA GTCAGGAACT CAAGACCAGC CTGGACAACA TGGTGAAACC  1079

CCATCTCTAC TAAAAATACA AAAAAATATC CAGGCGTGGT GGTGGGCGTC TGTAATCCCA  1139

GCTACTTGGG AGGCTGAGGC AGGAGAATCG CTTGAACCCA GGAGTCAGAG ATTGCGGTGA  1199

GCTAAGGTCG TGCCACTGCA CTCCAGCCTA GGCAACAAAA GCGAACCTCC GTCTCAAAAA  1259

AAAAAAAAAA AAAAAAAA                                               1278
```

(2) INFORMATION FOR SEQ ID NO:5:

(i) SEQUENCE CHARACTERISTICS:
        (A) LENGTH: 1242 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (B) CLONE:F335

(ix) FEATURE:
        (A) NAME/KEY: CDS
        (B) LOCATION: 593 to 742
        (C) IDENTIFICATION METHOD: by experiment (xi) SEQUENCE DESCRIPTION: SEQ ID NO:5:

```
GAATTCGGCA CGAGCCTTTT TGTAACCCTG AGCCATAAAT TCCCTTTCTT TCTCATTTAA    60

ACACACTGAA GTACCATCTA AGTATGTGAG AACTGTGAAA GGAGCACCTG TCACAACACC   120

TAAGTCCTTA ATGCTTTGCT CATCCAAGTT GGAGTGTACT AATAATGTGA TTTTTCACAT   180

AATAATGGCA AAAATAAGTA AAAAGTAGCT TAGGAGGTGC AGAGAGACTT ATAAAAAGAA   240

GTATAACCAC CTATGGCACC AAATATCAAA CAGATTACAT AAAAACCATT TTTCTTATAA   300

TCCGTGTCTT TTTTTCTGGG TTTTTCTCTT GCTCTGGTTT GGTGGACTGA CTTTAAGCTG   360

ACCTCCAGTC CTTATGCCCT CACGTAATTC CCTTGTGTTG AGTGTGGGCT GGTCTGGTTC   420

TAACCAATAG AACATACCAA AGGTTATGGA TTGTCATTTT CATGACTAGG TTGCAAGAGA   480

CAGTAACTTC TGGTTAGCTA GTAGACTCCC TTGCTGGCTT TTATGAAGGA TACTGCTATG   540

TTGTGAGTGA TCCTATGGAG AAGTCCATGT GATAAGGGAC TGAGGGTAGC TT ATG GCT   598
                                                        Met Ala
                                                         1

GGC AGC CAA CAA GGA ACT AAG ATT CTC GGT TCA AAA CAT AGA AAA ACC    646
Gly Ser Gln Gln Gly Thr Lys Ile Leu Gly Ser Lys His Arg Lys Thr
      5                  10                  15

AAA TCC TGC CAA CAC TTG TGT GAC CTC ACT TTC TGG CTG AGC CTT TGG    694
Lys Ser Cys Gln His Leu Cys Asp Leu Thr Phe Trp Leu Ser Leu Trp
 20                  25                  30

ATG ATA TGC ACC TTG CCC ATC GCC TTG ATT ATA GCC TGT GAG AAA CCC    742
Met Ile Cys Thr Leu Pro Ile Ala Leu Ile Ile Ala Cys Glu Lys Pro
 35                  40                  45                  50

TGAAGCAGAA ACCCCAGCTA AGATACATCT GAACTCCTGA CCAAAAGAAA CTGTGAGATA   802

ATAAATACGT GTTGTTTTAA GATGTTAAAT TTGTGGTAAT TTGTCCTGCT GTAATAGAAA   862

TAATTTTAAA ATTGTTTTAG GGAAGATCTG TGAGTGGCAC ACTGATCTTT TGTGAGGCTA   922

AAAAGTATTT TTTTGGCCGG ATGCAGTGGC TCGTGCCTGT AATCCCAGCA CTTTGGGAGG   982

CCAAGACGGG CGGATCACTT GAAGTCGGGA GTTCGTGACC AGCCTGGCCA ATATGGTGAA  1042

ACCCCGTCTC TACTAAAAGT ACAAAAATTG GCTGGGCATG GTGGTGCGTG CCTGTGGTCC  1102

CAGCTGCTTG GGAGGCTGAG GCGGGAGAAT CACTTGAAAC TCCGAGGCGG AACTTGCAGT  1162

GAGGCGAGAT CAAGCCACTG CACTCCAGCA TGGGCAATGA GCGAGACTCC GTCTCAAAAA  1222

AAAAAAAAAA AAAAAAAAA                                              1242
```

(2) INFORMATION FOR SEQ ID NO:6:

(i) SEQUENCE CHARACTERISTICS:
    (A) LENGTH: 1342 base pairs
    (B) TYPE: nucleic acid
    (C) STRANDEDNESS: double
    (D) TOPOLOGY: linear (ii) MOLECULE TYPE: cDNA to mRNA (vi) ORIGINAL SOURCE:
    (A) ORGANISM: human (vii) IMMEDIATE SOURCE:
    (B) CLONE:F547

(ix) FEATURE:
    (A) NAME/KEY: CDS
    (B) LOCATION: 591 to 719
    (C) IDENTIFICATION METHOD: by experiment (xi) SEQUENCE DESCRIPTION: SEQ ID NO:6:

```
GAATTCGGCA CGAGAAGATG ATTCAAGATT TGTGCCGGAC AAGGAGAAAA AGAAAATTTG   60

TTGATATCTT TGGGTGAGGA TGGAGAGGTC CAAGAAACCA TTTTGCAAAT GTTTTATATT  120

ACTAACAAGA CAATCTAAAC CTAAATAAAC ATCTTTTTCA GAGAAAAGAC ACTAGAGAAA  180

GATTTAATTT GTGATATTTC AAGCTAGATT ATAAACTGTG ATCTTTGTGA ATGAATTAAT  240

TCATTCCAGA ATTAAATTTT GGTCTTTGTA TTTTGATTCC TTTTACTTTA GTGAGGATTT  300

TGTAGAGAAG ATGAAATTTC ACCTCTATAA TAATAGAAGT TAGGAGTGAG GTCTCACAAA  360

CATGGGCTGT CTTCTAGATT TGGGATATAC CATCAGAGAC AATAAATAAC TGAAATTTGG  420

AAACTGGATA AAAGAGTCTG CTAGTTAGGA CCACTTGACT AAGAGTGGGT ATAGAAGAAA  480

CCTAAGGAAG AAAAGTTAGA TTTGAGACAA CATATTGGAG TATGTTGAAA TTAAAGGTGA  540

ATAAAGTAGT GGAAATTCGA TAGAATTTAA AGGAGACATT GTAGTGGGAG ATG GTA     596
                                                       Met Val
                                                        1

GAG GTG ATT AGA TAT AAT ATG TAT ATT TAT TTG AAA AAT AGA TAT ATA    644
Glu Val Ile Arg Tyr Asn Met Tyr Ile Tyr Leu Lys Asn Arg Tyr Ile
        5                   10                  15

AGA ATG AAA GTT GTA TGT AGT ACC AAC AAG TAC CAT TCG TAT TAT GAT    692
Arg Met Lys Val Val Cys Ser Thr Asn Lys Tyr His Ser Tyr Tyr Asp
 20                  25                  30

TCA CAA TTT ACA GAG TAT TTT CAT ATA TAAAAATCTT GTGCAATGGG          739
Ser Gln Phe Thr Glu Tyr Phe His Ile
 35                  40

TTGTTTTTTC ATTTTATAGA AGGAGCAGAG GCTAAAGGAA GTTGAGGTTA AGTGATTTGG  799

AAGTTACAAA AACTAGTAAG AGCTCAAACT AGCAATAAAA TTATAGTATG TTTTTCCCTT  859

GCCTTCACTG TAATGCTTAA TGGTTGTGTA GTCTTATACG TGACTCCTGA CTTCAAGGAT  919

CCTGGTCTGT ACCTCTTTAG GTCAACACGT TTTGAGTGAA CTGGTGTTGG TTATTTGGAA  979

TTAGATATAA AGTCATATAT TCTTTGGTGA GGAATGGCTT CATATAGGAG TTCACATTCA 1039

AAACAAGCTT TGACAAAATA ATAGAGTGAA AATTGGTAGA TCAGAGTTGA GCTGATTGGA 1099

GGACCAAATT AAAAGACTGG CTGGGCATGA TGGCTCACAC CTGAAAACCC AGCACTTTGG 1159

GAGGCCAAGG CAGGCAGATT GTTTGAGCCC AGGAATTCAA GACCAGCCTA GATAACCTGG 1219

GTATCCCAGC TACTTGGGAG GCTGAGCTGC CGAGGCTACA GTGAGCCATG ATCGTGCCAT 1279

TGCTTTCTAG CCTGGGTGAC AGATTGAGAC CCTGTCTCAA AAAAAAAAA AAAAAAAAA  1339

AAA                                                              1342
```

(2) INFORMATION FOR SEQ ID NO:7:

```
            (i) SEQUENCE CHARACTERISTICS:
                (A) LENGTH: 3527 base pairs
                (B) TYPE: nucleic acid
                (C) STRANDEDNESS: double
                (D) TOPOLOGY: linear (ii) MOLECULE TYPE: cDNA to mRNA (vi) ORIGINAL SOURCE:
                (A) ORGANISM: human (vii) IMMEDIATE SOURCE:
                (B) CLONE:F998

(ix) FEATURE:
                (A) NAME/KEY: CDS
                (B) LOCATION: 140 to 1084
                (C) IDENTIFICATION METHOD: by experiment (xi) SEQUENCE DESCRIPTION: SEQ ID NO:7:

GAATTCGGCA CGAGTAGATA TTCTCTACGT CAAAGACTTG GCCTTTGTGG ACCCCGATGA      60

CTGCACCCCC CTCAAGACTA TCACTCGCTT CTATAACCAC CCGGTGCACT TTGTCTTCCA    120

TGACACCAAG TTGGATGCC ATG CTG GAG GAG TTC AAG AAG GGG AAG TCC CAC    172
                       Met Leu Glu Glu Phe Lys Lys Gly Lys Ser His
                         1               5                      10

CTG GCC ATC GTG CAG AAG GTA AAC AAC GAG GGT GAG GGT GAC CCC TTC     220
Leu Ala Ile Val Gln Lys Val Asn Asn Glu Gly Glu Gly Asp Pro Phe
             15                  20                  25

TAC GAG GTC CTG GGC CTG GTC ACC CTG GAG GAC GTG ATC GAG GAG ATC     268
Tyr Glu Val Leu Gly Leu Val Thr Leu Glu Asp Val Ile Glu Glu Ile
         30                  35                  40

ATC AAG TCG GAG ATC CTG GAC GAG TCC GAC ATG TAC ACT GAC AAC CGA     316
Ile Lys Ser Glu Ile Leu Asp Glu Ser Asp Met Tyr Thr Asp Asn Arg
 45                  50                  55

AGC CGG AAG CGG GTG TCT GAG AAG AAC AAG CGT GAC TTC TCT GCC TTC     364
Ser Arg Lys Arg Val Ser Glu Lys Asn Lys Arg Asp Phe Ser Ala Phe
 60                  65                  70                  75

AAG GAT GCG GAC AAT GAG CTC AAA GTG AAA ATC TCC CCG CAG CTC CTC     412
Lys Asp Ala Asp Asn Glu Leu Lys Val Lys Ile Ser Pro Gln Leu Leu
                 80                  85                  90

CTG GCC GCT CAT CGC TTC CTA GCC ACA GAG GTC TCT CAG TTT AGC CCC     460
Leu Ala Ala His Arg Phe Leu Ala Thr Glu Val Ser Gln Phe Ser Pro
             95                 100                 105

TCC CTG ATA TCA GAG AAG ATC CTG CTG CGG CTA CTC AAG TAC CCA GAT     508
Ser Leu Ile Ser Glu Lys Ile Leu Leu Arg Leu Leu Lys Tyr Pro Asp
        110                 115                 120

GTC ATT CAG GAA CTC AAG TTT GAC GAG CAC AAT AAG TAC TAC GCC CGC     556
Val Ile Gln Glu Leu Lys Phe Asp Glu His Asn Lys Tyr Tyr Ala Arg
    125                 130                 135

CAT TAC CTG TAC ACC CGA AAT AAG CCG GCC GAC TAC TTC ATC CTC ATC     604
His Tyr Leu Tyr Thr Arg Asn Lys Pro Ala Asp Tyr Phe Ile Leu Ile
140                 145                 150                 155

CTG CAG GGG AAG GTG GAG GTG GAG GCA GGG AAG GAG AAC ATG AAG TTT     652
Leu Gln Gly Lys Val Glu Val Glu Ala Gly Lys Glu Asn Met Lys Phe
                160                 165                 170

GAG ACG GGC GCC TTC TCC TAC TAT GGG ACT ATG GCC CTG ACC TCG GTC     700
Glu Thr Gly Ala Phe Ser Tyr Tyr Gly Thr Met Ala Leu Thr Ser Val
            175                 180                 185

CCC TCC GAC CGT TCC CCA GCA CAC CCC ACC CCA CTC AGC CGC TCA GCC     748
Pro Ser Asp Arg Ser Pro Ala His Pro Thr Pro Leu Ser Arg Ser Ala
        190                 195                 200

TCC CTC AGT TAC CCA GAC CGC ACA GAC GTC TCA ACT GCA GCA ACC TTG     796
Ser Leu Ser Tyr Pro Asp Arg Thr Asp Val Ser Thr Ala Ala Thr Leu
    205                 210                 215
```

```
GCA GGC AGC AGC AAC CAG TTT GGC AGC TCT GTC CTG GGC CAG TAC ATC      844
Ala Gly Ser Ser Asn Gln Phe Gly Ser Ser Val Leu Gly Gln Tyr Ile
220                 225                 230                 235

TCT GAC TTC AGC GTC CGG GCA CTC GTG GAC TTG CAG TAC ATC AAG ATC      892
Ser Asp Phe Ser Val Arg Ala Leu Val Asp Leu Gln Tyr Ile Lys Ile
                    240                 245                 250

ACT CGG CAG CAG TAC CAG AAC GGG CTG CTG GCT TCT CGC ATG GAG AAC      940
Thr Arg Gln Gln Tyr Gln Asn Gly Leu Leu Ala Ser Arg Met Glu Asn
                255                 260                 265

AGC CCT CAG TTT CCC ATA GAC GGG TGC ACC ACC CAC ATG GAG AAC TTG      988
Ser Pro Gln Phe Pro Ile Asp Gly Cys Thr Thr His Met Glu Asn Leu
            270                 275                 280

GCC GAG AAG TCT GAG CTG CCT GTG GTG GAC GAG ACC ACA ACT CTT CTC     1036
Ala Glu Lys Ser Glu Leu Pro Val Val Asp Glu Thr Thr Thr Leu Leu
        285                 290                 295

AAC GAG CGT AAC TCC TTG CTG CAC AAA GCC TCC CAC GAG AAT GCC ATC     1084
Asn Glu Arg Asn Ser Leu Leu His Lys Ala Ser His Glu Asn Ala Ile
300                 305                 310                 315

TGACAGGAGG GCCCGGGGCC CCCTGCCCAC CCTGCGGGGG CCTCCCCAGT GGGCCCACAT   1144

GAAGAGAGGG AACCTGTTAG TCCAGAAAGG ATACGGATAG ATAGCCTGTC TGACTGAACA   1204

GCCAGATGGC CCCCAGCCTA TGGGGATCT GGCCTCTGCC AGGGACCTCT GAGTAGCTCT    1264

GAGGTGGCAC TGTCCAGCCC TGGATAGGGG GGGCAGTGGG CCAGCTACCG TAAGCAAAGG   1324

CTGTTTTTTA CTGAGAGAAT TTCTAAAGTA GGCTCATCAC TTTTTTTTAA ATATCATTTT   1384

GGGAAGGGAA GACAGGGTTA AGGAACTTTA TTTAAAAAAA AAATATTTTT TTCCTAAAAA   1444

CTATAAAAGA GGAAGGGTTT CTTGTCCCGG GAAGCAACGG ACATAATCTG TTCCCAGCCA   1504

TGGCCTTCCA GCTTGTGTCC CTGATTCAGG GAGCTCTCCC TTCCTCCTCC TCCTCCTCCT   1564

CCGGAGGTGG GATCCCAGAG CCTGCCAGTG GAGGCTTATC TGTTGGGAGG AAGACAGCTC   1624

TTCACAGAAG CAAAGAACAA AATGGCATGG AGATCAGCTG CCTGAGCACC TGCGCTGTAG   1684

CTTATCTGAC AACGCTGAGG CCACGAGCTC CTGGGTAGCT GTGATCAGGG ACATGATAAT   1744

CTGAGCTATG CAGAGGAGCA CATCTGTTGT CAACTGCTGT ACCCAGAAAT CTAGAACTCT   1804

GCCGACAGCC TCTCCTGGTG AGTCGGGACT CAGCTGAGGA CACATCCCCA CCCTGCCTCC   1864

CATCTGGCCC TTTGGACAAC TGGCCCTTTG TGACAGGGCT GACTCAAGTG TTAGGCAGGG   1924

TCTCAGGCCT TTGATTGCTC ACCCCTGCTC CCCAGGCCCT GCCCTCACTT TTACCAAAGG   1984

TTCTCCCTCG GCGGGAGGGC ATCTGTGTTG GAGGTGATTT GTCTGGGTTC TTCCTTTTGG   2044

TTCCAGAAGG AACTGTCAGT CATCAGCATC TGCGTTGTTA GCAGTCAGTA CCACCCCCGC   2104

CCCACAATGA CAGTCAAGGC TGACTTGTTG ACTGAAGCCT TTTTCCCAGA CCCCTTATTT   2164

CGAATCCCCA AGCTTCAGTC CCTCTTGGGG GTGGAGACAA GAGGACATGT GGGAAGCCAC   2224

GGAAGCAGGT TCTTTATGTC CTCTCCTCTG TGGCTGGCAA GGCTCACCTG GCCTTATCCA   2284

CCCACTTATG GAACCTCAGG AGAGGAGGGC TCCTCCTAAA GGCATGCAGC TTGCAGCCCC   2344

TCTTTCTCAC ACGTGTGATC CTAGCGTGAG AGGTCATCCT GCCCTTGCTG AAGTTAGTAG   2404

TACTGTACTA AGAGCTCTGC CCTCATGTGA ATTCCTGCCC TGGCGCCTCT TCCCTGGGGC   2464

TGAATCAGGC CCTGCTGCAA AACTCCAGGC TTCCCAGGGT TGGGGAGGCT GTGGGACCAA   2524

GGTCCATGTT GGTCCTTCCA CTGGGTGCAG CAGGAGCTGG GTCCCGAGAG CCTGGCAGGT   2584

GAAACTCTGC AGGCCTTCCG CCTGATTATT ATTTATTCAC TCCTTTCCTC ACCCCAAGTG   2644

CCCTGCTCTC CAGGTGCCTA GAGTATCCTA ACTCTTAGGA CCAGGGATTG TCTTGCACCA   2704

AGTATGCCTA CCCCTGGCCA GTCTGAGGTC TCCTAGCCAT AGAACTGACT CCTGGAAGCC   2764
```

-continued

```
TGGAGAGAAG GTGGTGACAC CCATGGGTTC TCAACTGTAA GGAAAAAAGA CACCAGACTT  2824

TTGTTCCCTA GTGGGGAAA GCCCTTAGTC TTGTACAGGA GCAGCTTGCT CCCAAGTCCT  2884

TTTGGAAGCT GGCAGAGCTA TATTCCTGAC AGCCCTGACT GCCAGGTAGA GCAAAAGACA  2944

TTGGTGGGGG TATGTGAAGC AAAAGGGGCA GGTGCACACA CCTCCACAGT GACCTCTGTG  3004

CACACGGTTA CCACCAACTG GCTGGCCCTC CTCCTCTTCC CTGGCCCATT GATCATCCCT  3064

TCTCACAGAG GGTCATCATT ATTTCCAAAT ATTGTTTGTC TGATGACTTC CTCTTCCCAG  3124

TGCAATTTTT CCCTTCCTAT TTCAACCTCT GGTTCCTGGG ATGAGCCATA CCCTGGAACT  3184

GGCCCACCCA CTGTGTCTTC CATGTAAGGG AGACCTTTGC AAAGGGCATC CAAATGGGTA  3244

GGCAGGTGAC AGCCGCCGTA TTTATTTTGC ATAATATTTT AATTTGTATA TTTTTGTGAT  3304

TTATTTTGGC GTTATGAGTT TGACTCTCGG GGAGTTTTGT TGTTATGACT CTTGTGTCTT  3364

TTGTCACAAA ACAATGATAT TTGCTAAACG ATATATGGAA TTTATTTTTG ATTGGTAATA  3424

AAAAATCAAA TATGTATAAA TCCTGGTGAA TCTAAAAAAA AAAAAAAAAA AAAAAAAAA  3484

AAAAAAAAAA AAAAAAAAAA AAAAAAAAAA AAAAAAAAAA AAA                  3527
```

(2) INFORMATION FOR SEQ ID NO:8:

(i) SEQUENCE CHARACTERISTICS:
        (A) LENGTH: 1512 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (B) CLONE:F1148

(ix) FEATURE:
        (A) NAME/KEY: CDS
        (B) LOCATION: 78 to 155
        (B) LOCATION: 618 to 725
        (B) LOCATION: 884 to 1018
        (C) IDENTIFICATION METHOD: by experiment (xi) SEQUENCE DESCRIPTION: SEQ ID NO:8:

```
GAATTCGGCA CGAGGAGAGA AAGAAAAAGA GAAAGAAAAA AAGAAAGAGG AAGGAAAGAA   60

GGAAGGAAGG AAGGAAA ATG GAG GCA TTA CAG CTG ATA CCA CAG GAA TAC     110
                   Met Glu Ala Leu Gln Leu Ile Pro Gln Glu Tyr
                    1               5                  10

AAA AGA TTA TTT AAG ACT ACT ATG AAC ACC TCT GTG CAC ATA AAC        155
Lys Arg Leu Phe Lys Thr Thr Met Asn Thr Ser Val His Ile Asn
          15                  20                  25

TAGAAAATCT ATAGGGAATT AATAAATTCC TGGAAACATA CCACCTCCCC AGCTTGAATC  215

AGAATGAAAC AGAAATTCTG AACAGACCAA CAACAAGCAG TGAGATTGAA TCAGTAATTT  275

AACAAAGTTG TCCTCCTAAA AAAAGCCAAG GGCCATACAA ATTCACAGCC AAATTCTACC  335

AGACATTCAA AGAATTGGCG CCAATTTTGC TGAAACTATT CTAAAAGACT GAGAAAGAAG  395

GAATCCTTCC TAACTCATTC TATGAAGCCA GTATCACCTT GATACCAAAG CCAGGAAAGG  455

GCATACAAAA CAAAACAAAC AAAAAACAAA AAAACACAAA ACGACAGACC AATATTCCTG  515

ATTAACATAG ATGCAGAAAT CTTCAACAAA ATACTAGCAA ACTAAACCCA ACAGCACATC  575

AAAAAGGTAA TTAACTATGA TTAAGTGGGT ATTATCCCAG GG ATG CAG GGA TGG    629
                                              Met Gln Gly Trp
                                               1
```

```
TTC AAC ATA TGC AAG TCA ATA AAT GTG ATT CAC CAT GTA AAC AGA ATT      677
Phe Asn Ile Cys Lys Ser Ile Asn Val Ile His His Val Asn Arg Ile
  5                  10                  15                  20

AAA AAC AAA AAC CAT ATG ATT ATC TCA ATA GAT GCA AAA AGC ATT GGA      725
Lys Asn Lys Asn His Met Ile Ile Ser Ile Asp Ala Lys Ser Ile Gly
                    25                  30                  35

TAAAATACAG CATCCTTTTA TAAACCCTC AACAAATTAG ATATAGAAGG AACATATCTC     785

AAAATAATAA AAGCTACATA TGGAAAACCA CAGCCAACAT CATACAGAAT AGGAAGAAGT    845

CAAAAGCATT CCCCCCTAAG AACTGGAATA AGACAAGG ATG CCC ACT TTT ACC ACT    901
                                       Met Pro Thr Phe Thr Thr
                                         1                 5

TCT ATT CAA TAT AGT ACT GGA AGT CAT AGC CAG GCC AAT CAG TCA AGA      949
Ser Ile Gln Tyr Ser Thr Gly Ser His Ser Gln Ala Asn Gln Ser Arg
             10                  15                  20

GAA AGA AAG GAA TTC CAA ATC AGA AAA GAG GAA GTC AAA CTA TTT ATA      997
Glu Arg Lys Glu Phe Gln Ile Arg Lys Glu Glu Val Lys Leu Phe Ile
                     25                  30                  35

TTT GCC GAC GAT ATG ATT GTG TAACTAGAAA AACCTAAAGA TCCCTCCAAA        1048
Phe Ala Asp Asp Met Ile Val
                 40              45

AGACTCCTAG ATTTGAGAAA TGAATTCAGT AAAGTCTCAG GTTACAAAAT CCATGTACAC   1108

AAATCAGTAG CTCTGCTGCA TGCCAACAAC GACCAAGCTG AGAATCAAAT AAAAAACTCA   1168

GTCCCTTATA TAATAGCTGA AAAAAAAAAA ACCTAGGAAT ACATTTAACT GGGGAGGTGA   1228

AAGAGCTCTA CAAGGAGGAC TACAAAACAC CACTGAAAGG AATCACAGAT GATACAAACA   1288

AATGGAAATA CGTGTCATGC TCATGGATTG GAAGAATCAG TATCACACAA ATGATCTAT    1348

TGCTCAAAGG AAGCTTCATA TTCACTGAAA TTCCTATCAA AATACCAAAT TATTTTTCAC   1408

AAAATTAGAA AAAAAATCCA AAAATTCATA TGGAACCAAA AAAAAAAAAA AAAAAAAAAA   1468

AAAAAAAAAA AAAAAAAAAA AAAAAAAAA AAAAAAAAAA AAAA                    1512

(2) INFORMATION FOR SEQ ID NO:9:

(i) SEQUENCE CHARACTERISTICS:
        (A) LENGTH: 882 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
         (A) ORGANISM: human (vii) IMMEDIATE SOURCE:
         (B) CLONE:F1180

(ix) FEATURE:
         (A) NAME/KEY: CDS
         (B) LOCATION: 97 to 195
         (C) IDENTIFICATION METHOD: by experiment (xi) SEQUENCE DESCRIPTION: SEQ ID NO:9:

GAATTCGGCA CGAGCTTAAT CTATGCAGTA CACTACTTCT TTTCAAAACT GCAGATCACG     60

GGAACAGCAA GCACAATTCT GTACTTTGGT TATACC ATG ATA ATG GTT TTG ATC     114
                                       Met Ile Met Val Leu Ile
                                         1                 5

TTC TTT CTT TTT ACA GGA ACA ATT GGC TTC TTT GCA TGC TTT TGG TTT     162
Phe Phe Leu Phe Thr Gly Thr Ile Gly Phe Phe Ala Cys Phe Trp Phe
             10                  15                  20

GTT ACC AAA ATA TAC AGT GTG GTG AAG GTT GAC TGAAGAAGTC CAGTGTGTCC    215
```

```
Val Thr Lys Ile Tyr Ser Val Val Lys Val Asp
         25                  30

AGTTAAAACA GAAATAAATT AAACTCTTCA TCAACAAAGA CCTGTTTTTG TGACTGCCTT  275

GAGTTTTATC AGAATTATTG GCCTAGTAAT CCTTCAGAAA CACCGTAATT CTAAATAAAC  335

CTCTTCCCAT ACACCTTTCC CCCATAAGAT GTGTCTTCAA CACTATAAAG CATTTGTATT  395

GTGATTTGAT TAAGTATATA TTTGGTTGTT CTCAATGAAG AGCAAATTTA AATATTATGT  455

GCATTTGTAA ATACAGTAGC TATAAAATTT TCCATACTTC TAATGGCAGA ATAGAGGAGG  515

CCACATTAAA TAATACTGAT GAAAGGCAGG ACACTGCATT GTAAATAGGA TTTTCTAGGC  575

TCGGTAGGCA GAAAGAATTA TTTTTCTTTG AAGGAAATAA CTTTTTATCA TGGTAATTTT  635

GAAGGATGAT TCCTATGATG TGTTCACCAG GGGAATGTGG CTTTTAAAGA AAATCTTCTA  695

TTGGTTGTAA CTGTTCATAT CTTCTTACTT TTCTGTGTTG ACTTCATTAT TCCCATGGTA  755

TTGGCCTTTT AAACTATGTG CCTCTGAGTC TTTCAATTTA TAAATTTGTT ATCTTAATAA  815

ATATTATAAA AATGAAAAAA AAAAAAAAAA AAAAAAAAAA AAAAAAAAAA AAAAAAAAAA  875

AAAAAAA                                                            882

(2) INFORMATION FOR SEQ ID NO:10:

(i) SEQUENCE CHARACTERISTICS:
        (A) LENGTH: 1837 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (B) CLONE:F1243

(ix) FEATURE:
        (A) NAME/KEY: CDS
        (B) LOCATION: 225 to 389
        (B) LOCATION: 977 to 1111
        (B) LOCATION: 1588 to 1698
        (C) IDENTIFICATION METHOD: by experiment (xi) SEQUENCE DESCRIPTION: SEQ ID NO:10:

GAATTCGGCA CGAGCAGAGA TTCTATCACC ACTGTCCGGT CTTTCTTGGA TGATTTTGAG   60

TCAAAGTATT CCTTCCATCC AGTAGAAGAC TTTCCTGCTC CAGAAGAATA TAAACACTTT  120

CAGAGGATAT ATCCCAGCAA AACAAACCGA GCTGCCCGTG GAGCCCCACC TCTGCCACCC  180

ATTCTCAGGT GAAGCCTGGC TTGGTCCCGT TCCTCAGGAA AAGG ATG GAC CTT CTC   236
                                                 Met Asp Leu Leu
                                                   1

TTC TTC TCA GAT GGT CCC TTC CAT TCC CCT GAA ACC TGC ATG AGA GCT   284
Phe Phe Ser Asp Gly Pro Phe His Ser Pro Glu Thr Cys Met Arg Ala
 5               10                  15                  20

CCT AAC ATG TTT CTC CAA TGC AAT CAA GCC CTA GAC TCC AAA TGT CCT   332
Pro Asn Met Phe Leu Gln Cys Asn Gln Ala Leu Asp Ser Lys Cys Pro
                 25                  30                  35

CCC AGC TCA CCT CCA TCT ATG CAT CTC ATC TCT GGA TTT GGT GAT CAG   380
Pro Ser Ser Pro Pro Ser Met His Leu Ile Ser Gly Phe Gly Asp Gln
             40                  45                  50

ACT CTA TAT TGACAGTAGG ATCTCAAACC CTGCATCCAT CCTTCCTCCA            429
Thr Leu Tyr
        55

GCAAGCCCTG CTAGCCACAT GAGGAACAAG TTTCCGTGTC TTCTGCCTTC CTCTTGGGGA  489
```

```
AAGGTGCCTT GTTGTGATGA ATTAACTCAC TGTTAGGGCA GGGTGGAGAA TGGTACTCCT   549

TCCTTCTCCT GTCCACTGTG GGGGAAGCTT GGCAGGTATA TTATATTTCA TCATTTAGGA   609

GGCTGGCATG ACCAGGACTT ATGGGTGGGA GGGGAGCATT TTTAGTGAAG CAAGAAAGGA   669

GTTTGCCAAG AAGTGATCTG TTTTAAAGGT CATATTTGGA GAAAGGGCAA GGAATTGGGT   729

CTGCTTTATT TTTGGGGGTA TTTTGTTTTT GTTCTCACCT GCTGCCCCCC CACCCCACCA   789

CCCCAGGGAT AAATTGGATA TAAACACTAA ATACTAATCA GTTGAACTTA ACATTTAATA   849

AAAGAAAGG GTGAAATAAA CTGAAGACCA TTTTAGAACT AGTCAGTTCT CTGCAGCAAA    909

GGGAACAGGA GCCATTTGAA CCCTCTGGGA CCCCTCACCC CACTGCTTCA GGGTGCTAGG   969
```

```
CTGAGGG ATG TTT TTC CTC CCC CTT ACC GCC CAT GCC CTT AAA AGA AAA   1018
        Met Phe Phe Leu Pro Leu Thr Ala His Ala Leu Lys Arg Lys
         1               5                  10

GTC ACT TTT TGT GGA GGG CAT CAT TCA TTC CTG ATT CAC AAA CCC CAA   1066
Val Thr Phe Cys Gly Gly His His Ser Phe Leu Ile His Lys Pro Gln
 15              20                  25                  30

AAA CCT CTG GTG GGA GAT AGG AAG ATA GGG CGT GGG CCT GGG CCT       1111
Lys Pro Leu Val Gly Asp Arg Lys Ile Gly Arg Gly Pro Gly Pro
             35                  40                  45
```

```
TAACCTCAAT CTTGTGTCTG CCTCAGTCTT TTCTGACTGG CCCTGAAGTT GTCAGTGGCT  1171

CTTTCTGTCC TTCAGCCCCT GGAAGGTGCT CCAGGATAAC AAAGAAGGGC AGGTTGAAGC  1231

CCCTCATGGA AGGAGCTGGC TTTGTGGGGC TGCAAAGGAC TTTTAAGTCC TGCCTGTACT  1291

GAAGTTCACA GCCCACCTGA CTGAGCAGAC TCTTCCTGTT CCTTTCTCTA CCACCCTTGC  1351

CTTCCCAGGA CTGCACGGTT AACACAGCA GAGTACAGAA GGGTGAAGAA GTGAGCAGAG   1411

GCTTATGAAG ATATTCAGAT ACTCTTCTAT GCCAGGAAGC ACAAAGACTT TGTTGAGATT  1471

TGCCTCAGTT CAGTAGATCT TCCTTGGCAG CCAGCCATAG GTTGTTTCTT TGTCTTCCGG  1531

GTCCTAAAGA GCACAGAAA AATGGAGGTC CCCAGTCTAG GTAGGAAGCT GATTGG ATG   1590
                                                              Met
                                                                1

AGG ACT TCT TTT TTT CCG ACA GCA GGA TGG GGC TCT TGG GCT CCA CAC  1638
Arg Thr Ser Phe Phe Pro Thr Ala Gly Trp Gly Ser Trp Ala Pro His
         5                  10                  15

ACC AGA TGC TTT GGT TTT CTA CAA CTG TTG CTA TGT GTA GAG GGT GCT  1686
Thr Arg Cys Phe Gly Phe Leu Gln Leu Leu Leu Cys Val Glu Gly Ala
         20                  25                  30

CAG AGC GTG GCA TGAGAGCAAG GAGACCATGG CTACTCTTTG AAATGGATGG       1738
Gln Ser Val Ala
         35

GGAAAATTAG CTTAAAAATT TAATCACGAG ATTGCGCCAC TGCACTCCAG CCTGGGCGAC  1798

AGAGCCAGAC TCCGTCTCAA AAAAAAAAAA AAAAAAAA                          1837
```

(2) INFORMATION FOR SEQ ID NO:11:

(i) SEQUENCE CHARACTERISTICS:
        (A) LENGTH: 1858 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (B) CLONE:F2232

(ix) FEATURE:
    (A) NAME/KEY: CDS
    (B) LOCATION: 26 to 1255
    (C) IDENTIFICATION METHOD: by experiment (xi) SEQUENCE DESCRIPTION: SEQ ID NO:11:

```
GAATTCGGCA CGAGGCCGCG CGAAC ATG GCG GCC GAA ATC CAC TCC AGG CCG      52
                             Met Ala Ala Glu Ile His Ser Arg Pro
                              1               5

CAG AGC AGC CGC CCG GTG CTG CTG AGC AAG ATC GAG GGG CAC CAG GAC     100
Gln Ser Ser Arg Pro Val Leu Leu Ser Lys Ile Glu Gly His Gln Asp
 10              15                  20                      25

GCC GTC ACG GCC GCG CTC CTC ATC CCC AAG GAG GAC GGC GTG ATC ACG     148
Ala Val Thr Ala Ala Leu Leu Ile Pro Lys Glu Asp Gly Val Ile Thr
                 30              35                  40

GCC AGC GAG GAC AGA ACC ATC CGG GTA TGG CTG AAA AGA GAC AGT GGT     196
Ala Ser Glu Asp Arg Thr Ile Arg Val Trp Leu Lys Arg Asp Ser Gly
             45                  50                  55

CAA TAC TGG CCC AGC ATT TAC CAC ACA ATG GCC TCT CCT TGC TCT GCT     244
Gln Tyr Trp Pro Ser Ile Tyr His Thr Met Ala Ser Pro Cys Ser Ala
         60                  65                  70

ATG GCT TAC CAT CAT GAC AGC AGA CGG ATA TTT GTG GGC CAG GAT AAT     292
Met Ala Tyr His His Asp Ser Arg Arg Ile Phe Val Gly Gln Asp Asn
     75                  80                  85

GGA GCT GTA ATG GAA TTT CAC GTT TCT GAA GAT TTT AAT AAA ATG AAC     340
Gly Ala Val Met Glu Phe His Val Ser Glu Asp Phe Asn Lys Met Asn
 90                  95                 100                 105

TTT ATC AAG ACC TAC CCA GCT CAT CAG AAC CGG GTG TCT GCG ATT ATC     388
Phe Ile Lys Thr Tyr Pro Ala His Gln Asn Arg Val Ser Ala Ile Ile
                110                 115                 120

TTC AGC TTG GCC ACA GAG TGG GTG ATC AGT ACC GGC CAC GAC AAG TGT     436
Phe Ser Leu Ala Thr Glu Trp Val Ile Ser Thr Gly His Asp Lys Cys
            125                 130                 135

GTG AGC TGG ATG TGC ACG CGG AGC GGG AAC ATG CTC GGG AGG CAC TTC     484
Val Ser Trp Met Cys Thr Arg Ser Gly Asn Met Leu Gly Arg His Phe
        140                 145                 150

TTC ACG TCC TGG GCT TCG TGT CTG CAA TAT GAC TTT GAC ACT CAG TAT     532
Phe Thr Ser Trp Ala Ser Cys Leu Gln Tyr Asp Phe Asp Thr Gln Tyr
    155                 160                 165

GCT TTC GTT GGT GAT TAT TCT GGG CAG ATC ACC CTG CTG AAG CTT GAA     580
Ala Phe Val Gly Asp Tyr Ser Gly Gln Ile Thr Leu Leu Lys Leu Glu
170                 175                 180                 185

CAG AAC ACG TGT TCA GTC ATC ACA ACC CTC AAA GGA CAT GAA GGT AGT     628
Gln Asn Thr Cys Ser Val Ile Thr Thr Leu Lys Gly His Glu Gly Ser
                190                 195                 200

GTC GCC TGC CTC TGG TGG GAC CCT ATT CAG CGG TTA CTC TTC TCA GGA     676
Val Ala Cys Leu Trp Trp Asp Pro Ile Gln Arg Leu Leu Phe Ser Gly
            205                 210                 215

GCA TCT GAC AAC AGC ATC ATC ATG TGG GAC ATC GGA GGA AGG AAA GGC     724
Ala Ser Asp Asn Ser Ile Ile Met Trp Asp Ile Gly Gly Arg Lys Gly
        220                 225                 230

CGG ACG CTG TTA CTT CAG GGC CAT CAT GAC AAG GTG CAG TCG CTG TGC     772
Arg Thr Leu Leu Leu Gln Gly His His Asp Lys Val Gln Ser Leu Cys
    235                 240                 245

TAC CTT CAG CTC ACC AGG CAG CTC GTC TCC TGT TCC TCG GAC GGC GGA     820
Tyr Leu Gln Leu Thr Arg Gln Leu Val Ser Cys Ser Ser Asp Gly Gly
250                 255                 260                 265

ATT GCA GTG TGG AAC ATG GAT GTT AGC AGA GAA GAG GCT CCT CAG TGG     868
Ile Ala Val Trp Asn Met Asp Val Ser Arg Glu Glu Ala Pro Gln Trp
                270                 275                 280

TTG GAA AGT GAT TCT TGT CAG AAA TGT GAG CAG CCA TTT TTC TGG AAC     916
```

```
         Leu Glu Ser Asp Ser Cys Gln Lys Cys Glu Gln Pro Phe Phe Trp Asn
                 285                 290                 295

ATA AAG CAG ATG TGG GAC ACC AAG ACG CTG GGG CTA AGA CAA CAT CAC         964
Ile Lys Gln Met Trp Asp Thr Lys Thr Leu Gly Leu Arg Gln His His
        300                 305                 310

TGC AGG AAA TGC GGG CAG GCT GTC TGC GGG AAG TGC AGC AGC AAG CGC        1012
Cys Arg Lys Cys Gly Gln Ala Val Cys Gly Lys Cys Ser Ser Lys Arg
        315                 320                 325

TCA AGT TAC CCA GTC ATG GGC TTC GAG TTC CAA GTC CGG GTT TGT GAT        1060
Ser Ser Tyr Pro Val Met Gly Phe Glu Phe Gln Val Arg Val Cys Asp
330                 335                 340                 345

TCT TGT TAC GAC TCC ATC AAA GAT GAA GAT CGG ACT TCT CTA GCG ACC        1108
Ser Cys Tyr Asp Ser Ile Lys Asp Glu Asp Arg Thr Ser Leu Ala Thr
                350                 355                 360

TTT CAT GAA GGA AAA CAT AAC ATT TCC CAC ATG TCC ATG GAC ATT GCC        1156
Phe His Glu Gly Lys His Asn Ile Ser His Met Ser Met Asp Ile Ala
            365                 370                 375

AGG GGA CTG ATG GTG ACC TGT GGG ACC GAC CGC ATT GTA AAG ATC TGG        1204
Arg Gly Leu Met Val Thr Cys Gly Thr Asp Arg Ile Val Lys Ile Trp
        380                 385                 390

GAC ATG ACA CCT GTG GTG GGC TGC AGT CTG GCG ACT GGG TTT TCT CCG        1252
Asp Met Thr Pro Val Val Gly Cys Ser Leu Ala Thr Gly Phe Ser Pro
        395                 400                 405

CAC TGATCTGAGA GCTGGGCGGC GTCCACACCT AAGAACAGCA GCTCCACCAA             1305
His
410

ATGAAGTCCC TCTCACGCAG CTCCACAGCG CTGTCTCGTG AATGGACAGT AGCCACTTAC      1365

AAACAAATCA ACATTTTTAA AAAGAAAATG TAAAGAGATG GGGTCTTGCC AGGTCTTGGC      1425

CAGGCTGGTC TTAACTCCCG GACTCAAGCA ACTCTCCTGA CTTGGCCTCC CAAAGTGTTG      1485

GAATTACAGG CATGAGCCAC TGCAGTAGCC CTGATTGTTT TAAATAGAAG AAGGTCTTTA      1545

GACAAACTCA ACCAATTGTC AACCAGAAAA TGTTGGAAGT TCCCTCCTAC CCCGCCCGCC      1605

TTTGAGTTGT CCGGCCTTTC TGGACCTAAC CAATGTATTT CTTAAATATA TTTGATTGAT      1665

GTCTCATGGC TCTTTAAATG TATAAAAGCA AGTTGTGCCC CAACCCCGGC CACCTTGGGC      1725

ACATGTTCTC AGGACCTCCT GAGGACTGTG TCCACAGGCC ATGGTCACTT ATATTTGGCT      1785

CAGAATAAAT CTTTTAAAAT AAAAAAAAAA AAAAAAAAAA AAAAAAAAAA AAAAAAAAAA      1845

AAAAAAAAAA AAA                                                         1858

(2) INFORMATION FOR SEQ ID NO:12:

(i) SEQUENCE CHARACTERISTICS:
        (A) LENGTH: 1082 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (B) CLONE:F3282

(ix) FEATURE:
        (A) NAME/KEY: CDS
        (B) LOCATION: 262 to 399
        (B) LOCATION: 621 to 713
        (C) IDENTIFICATION METHOD: by experiment (xi) SEQUENCE DESCRIPTION: SEQ ID NO:12:
```

```
GAATTCGGCA CGAGCGAACT CCTGAACTCA GGTAATCCTC TCACCTCAGC CTCCCGAAGT    60

GCTGGGATTA CGGGCGTGAG CCACTGTGCC TGGCCTGAGA GGACAAATAT TTTTAAAAAG   120

AAATGATAGT TCTTTATGTA TAGAATGTGG GATGATTTTT TTTTAATTGC CCTCGTTTTC   180

AGAACATGTA TTCAGTTTGA TCAGTGATTT TCAGTCTTGG CACTATTGAC ATTTAGGGTC   240

GGATAATCTC CAGGCTATCC T ATG CAT TGT AGG ATG TTC TGT AGC ACT CCT    291
                       Met His Cys Arg Met Phe Cys Ser Thr Pro
                        1               5                  10

GGC CAC TAC CCA CTA GAT AGG TCA GTA ACA CCT CTC CTC ACC CCC ACC    339
Gly His Tyr Pro Leu Asp Arg Ser Val Thr Pro Leu Leu Thr Pro Thr
                15                  20                  25

CTG ATT GTG ACT ACC AAA AAT GTC TCT AGA CAT TGC CAA ATG CCC TCT    387
Leu Ile Val Thr Thr Lys Asn Val Ser Arg His Cys Gln Met Pro Ser
            30                  35                  40

GGG GGG CAA ACG TGACCTCTGA TAAAATTCAC TGTCACTTAT GAAGATTCCT        439
Gly Gly Gln Thr
            45

TAATTATTTA TTTATGCCTT TTATGAACTA GGGTTCCCTT GATGTAAGCT AGGTACAGGT   499

GTTGAATGAA TCCCTTCTGC AGATGTAGTG TATAGCTTGG GCGGTGCCTG ATATATGTTG   559

GAGAACACTG GAATATGATG AAATATTTTA GCACTATTGG GAATTTAATT GAAGGTTCGA   619

A ATG AGC TCT TGT TTT GAA AGT AAA GGT GTA GGC TTT CTG CTG TAT CTA  668
  Met Ser Ser Cys Phe Glu Ser Lys Gly Val Gly Phe Leu Leu Tyr Leu
   1               5                  10                  15

AAT CTC TGT TTT CCA CCT CTG CCA CCA CCC CCT CAT GCA TTT GCT        713
Asn Leu Cys Phe Pro Pro Leu Pro Pro Pro Pro His Ala Phe Ala
                20                  25                  30

TGAAAAAGAT CCTTACTAGC TTAGGAATAG TTGAGAATTT CGTTTGAAAT GTTGACATG    773

ATCTGTCTAT ATCTTGTGTT CAAGGAAAGA TAGTTTTGTT TGTTTGCGTG TTTGTTTGTT   833

TTTGAGAACA GGGTCTTGCT CTGTTGCCCA GGTTGGAGTG CAGTGGCTCG ATCACAGCTC   893

ACTTCAGCCT CCACCTCCTG GACTTAAGAG ATTCTCCCAC CTCAGCCTGT TGAGTAGCTG   953

GGACTACAGA TGTGCATGCC ACCAACACTC TGCTAATTTT TCTACTTTTT ATAGAGATGA  1013

GATTTCACCA GCCTGGGAAA CATGGTGAGA CCCCCTCTCT ACCGAAAAAA AAAAAAAAA  1073

AAAAAAAAA                                                         1082

(2) INFORMATION FOR SEQ ID NO:13:

(i) SEQUENCE CHARACTERISTICS:
        (A) LENGTH: 1505 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (B) CLONE:F11037

(ix) FEATURE:
        (A) NAME/KEY: CDS
        (B) LOCATION: 575 to 703
        (B) LOCATION: 863 to  997
        (B) LOCATION: 1121 to 1345
        (C) IDENTIFICATION METHOD: by experiment (xi) SEQUENCE DESCRIPTION: SEQ ID NO:13:

GAATTCGGCA CGAGGTAGAA TTGACCCAGT GCTGCCCTGG CAACTTTGTA TATTAGGACA    60
```

```
AATTTACATT TCTTACCTTT ATGAGAGGCA CCCTGGTAGG CTAGTGGAGT TACACACAAA    120

GTCTGATCTC AGCTGCACTG TCCAGAAATG CAACACGGTC AATCAAATA ACATTCTCTG     180

AGCCTGTTTA TTTAGCTGTG AAAGAAGAAT AACATACCCA TCTAAAAAGG CAGCTTATTG    240

TATTTGATTG GTCTTTTATT TTCTATGAAA CTGTGTTTAA CACAGTAATT ATTTTCATTT    300

GTGTACTACA TTTGTGTTGT GTTTTTGGTT TTAGTTTTGT TTTTGAAATG GAGTCTTTTT    360

TTTAGTGGTT TTTTGTTTTG TTTTGTTTTG TTTTGTTTTT GAGATGGAGT CTTTCTATTG    420

CACTCCAGCC TGGGCAACGA GCAAAACTCT GTCTCAAAAT AAAAAAAAGA TTTCTTAAAA    480

TGATATTTTC AGTATTTTAT AGATGATGTG TAAGCAGCAA GCTTAATAGG ATGTTACCCG    540

ACACTTTGCG AGACTGGCAG CTGATTTGAT CCAG ATG TCT CTA ATT CTT TTT TCT    595
                                       Met Ser Leu Ile Leu Phe Ser
                                        1                5

TTT TCT TTT TCT GTT TTT TTT TTT GAC AGA GCC GAG ATC ACA CCA CTG      643
Phe Ser Phe Ser Val Phe Phe Phe Asp Arg Ala Glu Ile Thr Pro Leu
         10                  15                  20

CAC TCC AGC CTG GGT GAC AGA GCG AGG CTC CGT CTC AAA AAA AAA AAA      691
His Ser Ser Leu Gly Asp Arg Ala Arg Leu Arg Leu Lys Lys Lys Lys
 25                  30                  35

AAA AAA TTG TTT TAGCGCTGGG TTTCCCAAGG TGGGAGAGAC AGACCCAGCC          743
Lys Lys Leu Phe
 40

TGGAGCTGGC CCCTGGCCTG TGTGCTGACT TCTTGGGGTC CTCAAACCAC TGTATTTTTC    803

TGTTGAGCCT GTACTTGGGG AGAGATCAGT AGCATTTGAG GAAGTAAGAG AAAAGAATC     862

ATG GTA CCT CAG GGT TTC TTT CCC TTT ACT CGC TGG CAG CCA TTG TCT      910
Met Val Pro Gln Gly Phe Phe Pro Phe Thr Arg Trp Gln Pro Leu Ser
 1               5                   10                  15

GTG GGC ACC TCA TGT TTT TCC ACA CTC TAC TGG GCC GTG GAG GTA ACG      958
Val Gly Thr Ser Cys Phe Ser Thr Leu Tyr Trp Ala Val Glu Val Thr
             20                  25                  30

ATC ACC CAG GCC AGT CTC CTC TGC CTG GGA TGC GCC CTC TGAGAGGAGG      1007
Ile Thr Gln Ala Ser Leu Leu Cys Leu Gly Cys Ala Leu
             35                  40                  45

CCTAGCAGGG CAGGCTCCCT CTGGGCATCC CTGGATGCAG CCTCTGGACA CATGCCTCCT   1067

TTAAAGTGTC CGGGTGCAGC TCAGGTTGAG TGGAGGTAGA AGGAGAAACA GAC ATG      1123
                                                               Met
                                                                1

TTT ACC ACG CGT TTT CCA AAG CTC CTG ATC TTT CCC AAG ATT GTA ACT     1171
Phe Thr Thr Arg Phe Pro Lys Leu Leu Ile Phe Pro Lys Ile Val Thr
             5                   10                  15

GAA AAC TGC TGT CTC TTG TTT TGT TCG TTT TGG GGG TGG TGG TGC TGG     1219
Glu Asn Cys Cys Leu Leu Phe Cys Ser Phe Trp Gly Trp Trp Cys Trp
             20                  25                  30

CTG GGC CAT GCT TGT GAA GTG ATG TGT GTC TCT GAT TTA ACG GAT TCA     1267
Leu Gly His Ala Cys Glu Val Met Cys Val Ser Asp Leu Thr Asp Ser
         35                  40                  45

CTG TTT TCT CTG CTA ATT GAG AGA GCG TTA TTT ACA TTA TTT ATT TGT     1315
Leu Phe Ser Leu Leu Ile Glu Arg Ala Leu Phe Thr Leu Phe Ile Cys
 50                  55                  60                  65

TTT GAC ACA AGT GCT TTC AGT GTT TTA TCC TAGCTAATGG CTTCTTAAAG       1365
Phe Asp Thr Ser Ala Phe Ser Val Leu Ser
                 70                  75

GTAATAAAAC CCTTCCAACG TAATTGGTCA GATAAAACTT TTTTTCTTGT ATGCTTAAAT   1425

AAAGCAATTA GTGAAGCACT TCTAAAAAAA AAAAAAAAAA AAAAAAAAAA AAAAAAAAA    1485

AAAAAAAAAA AAAAAAAAA                                                1505
```

(2) INFORMATION FOR SEQ ID NO:14:

(i) SEQUENCE CHARACTERISTICS:
        (A) LENGTH: 232 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (B) CLONE:F427

(ix) FEATURE:
        (A) NAME/KEY: CDS
        (B) LOCATION: 17 to 178
        (C) IDENTIFICATION METHOD: by experiment (xi) SEQUENCE DESCRIPTION: SEQ ID NO:14:

```
CGCACAGTAA GGGAGA ATG TGG GGA CTC AGA GCA GGA GCC TTT GGA GTC AGA      52
               Met Trp Gly Leu Arg Ala Gly Ala Phe Gly Val Arg
                 1               5                  10

GAA GTT TTC CAG AAG GAA CAT CTA AGC AGA GCC CGG TTA GGC AAA GTG        100
Glu Val Phe Gln Lys Glu His Leu Ser Arg Ala Arg Leu Gly Lys Val
         15                  20                  25

AAC TGC CAT GGC GAG GGC CTG GAG ACT TCC AGN AGC GTG ATA ACT GCT        148
Asn Cys His Gly Glu Gly Leu Glu Thr Ser Ser Ser Val Ile Thr Ala
 30                  35                  40

CTT AAT TGT TCA ANC CTC ACC AGG AGC TAAGCCCTGT AAGGTGGGTG              195
Leu Asn Cys Ser Ser Leu Thr Arg Ser
 45                  50

CTATTAGGGT CCCCATTCTA CAGATGAGGA AACTGAA                               232
```

(2) INFORMATION FOR SEQ ID NO:15:

(i) SEQUENCE CHARACTERISTICS:
        (A) LENGTH: 196 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (vii) IMMEDIATE SOURCE:
        (B) CLONE:F981

(ix) FEATURE:
        (A) NAME/KEY: CDS
        (B) LOCATION: 67 to 102
        (C) IDENTIFICATION METHOD: by experiment (xi) SEQUENCE DESCRIPTION: SEQ ID NO:15:

```
CAAGTTCAGA TTAGAGAGGC CACTTTCCCA GAATCCACAG CTGCACTAAG NTAAGNGAGA      60

AGCCAG ATG CCG TTT TAC TGN GGT GTC AGG GGG CTG TTC TGAAGCTTGG          109
       Met Pro Phe Tyr Tyr Gly Val Arg Gly Leu Phe
         1               5                  10

GGGGGNTCAT TTTGAAAGGC CTTTCTTTCC CCTGGGGNAC CTNGGNTACC TTGGGGGACC      169

TACAAAGGTN GGTTGAGGGG AAGGGTG                                          196
```

(2) INFORMATION FOR SEQ ID NO:16:

```
       (i) SEQUENCE CHARACTERISTICS:
           (A) LENGTH: 522 base pairs
           (B) TYPE: nucleic acid
           (C) STRANDEDNESS: double
           (D) TOPOLOGY: linear (ii) MOLECULE TYPE: cDNA to mRNA (vi) ORIGINAL SOURCE:
           (A) ORGANISM: human (vii) IMMEDIATE SOURCE:
           (B) CLONE:F1984

(ix) FEATURE:
           (A) NAME/KEY: CDS
           (B) LOCATION: 37 to 198
           (C) IDENTIFICATION METHOD: by experiment (xi) SEQUENCE DESCRIPTION: SEQ ID NO:16:

GAATTCGGCA CGAGCAGCTG CAGCAGAAGA GCGGAA ATG TCA AAC GTG GAG AGC           54
                                        Met Ser Asn Val Glu Ser
                                         1               5

CTA AAG ATA GTA ATG AGC AGC TTG AGT CTT AAG TTT TTG AAT ACA CCG          102
Leu Lys Ile Val Met Ser Ser Leu Ser Leu Lys Phe Leu Asn Thr Pro
         10                  15                  20

ATG GAA GTT GAC AAA GAT TCT TTG CTT GGC CAA ACT TTA GTC AGA CTC          150
Met Glu Val Asp Lys Asp Ser Leu Leu Gly Gln Thr Leu Val Arg Leu
         25                  30                  35

CTC AAC CTT CTC GTA GGT TTA TCT GTG CAT TTC CTT GGA AAA TCC AGT          198
Leu Asn Leu Leu Val Gly Leu Ser Val His Phe Leu Gly Lys Ser Ser
 40                  45                  50

TAGAACCCTC TACCCTCAAT ATCTGATCAG GTTCCTCATC CTCTACCATC CAAGGTGATG        258

TCTGATCACC TTGACCTATT TTCAGCAAGA AACCCCTTTA CTCCTGAAGT TCCTTCTTAG        318

TAATTTTTTT ATCCAGTGAC CCCAAGCTTT TTGTTCCTTG GCTATAAATT CCCACTTGCC        378

CATGCTGTAT TTAGAGTTGA GCCCACTCTC TCTCTCCTAA TTCAGAATCC CATTGCCATG        438

GTTGCTATAC CTATCCTGAT GGTCCGGAAT AAAATCTGTC TTACTGTGCT TTAAAAAAAA        498

AAAAAAAAAA AAAAAAAAAA AAAA                                              522

(2) INFORMATION FOR SEQ ID NO:17:

(i) SEQUENCE CHARACTERISTICS:
           (A) LENGTH: 1908 base pairs
           (B) TYPE: nucleic acid
           (C) STRANDEDNESS: double
           (D) TOPOLOGY: linear (ii) MOLECULE TYPE: cDNA to mRNA (vi) ORIGINAL SOURCE:
           (A) ORGANISM: human (vii) IMMEDIATE SOURCE:
           (B) CLONE:F2593

(ix) FEATURE:
           (A) NAME/KEY: CDS
           (B) LOCATION: 640 to 1002
           (C) IDENTIFICATION METHOD: by experiment (xi) SEQUENCE DESCRIPTION: SEQ ID NO:17:

GAATTCGGCA CGAGGATCTC GCCGCGGTTC CGCGGCCCTG CCGCCGCCGC CGCCAGCAGA         60

GCGCACCGGG CCGATCGGGC GAGTGGCCAT GGCGGGCGCC GAGGACTGGC CGGGCCAGCA        120

GCTGGAGCTG GACGAGGACG AGGCGTCTTG TTGCCGCTGG GGCGCGCAGC ACGCCGGGGC        180

CCGCGAGCTG GCTGCGCTCT ACTCGCCAGT GCCCTTCACT CTCTGAAGAA CAGCCATGCC        240
```

```
TGAATCAGAG TCTGCAGACA GCCTGGTGCC CCAAATCTGC AATCAAGGCC CTTTATCTCC    300

TCCAGACCTG GAGGCAAGCG CCTCCAGGAG TGGTGCTCTG TGATCCTGTG CTTCAGCCTC    360

ATCGCCCACA ACCTGGTCCA TCTCCTGCTG CTGGCCCGCT GGGAGGACAC ACCCCTCGTC    420

ATACTCGGTG TTGTTGCAGG GGCTCTCATT GCTGACTTCT TGTCTGGCCT GGTACACTGG    480

GGTGCTGACA CATGGGGCTC TGTGGAGCTG CCCATTGTGG GAAGGCTTT CATCCGACCC     540

TTCCGGGAGC ACCACATTGA CCCGACAGCT ATCACACGGC ACGACTTCAT CGAGACCAAC    600

GGGGACAACT GCCTGGTGAC ACTGCTGCCG CTGCTAAAC ATG GCC TAC AAG TTC       654
                                            Met Ala Tyr Lys Phe
                                             1               5

CGC ACC CAC AGC CCT GAA GCC CTG GAG CAG CTA TAC CCC TGG GAG TGC      702
Arg Thr His Ser Pro Glu Ala Leu Glu Gln Leu Tyr Pro Trp Glu Cys
              10                  15                  20

TTC GTC TTC TGC CTG ATC ATC TTC GGC ACC TTC ACC AAC CAG ATC CAC      750
Phe Val Phe Cys Leu Ile Ile Phe Gly Thr Phe Thr Asn Gln Ile His
         25                  30                  35

AAG TGG TCG CAC ACG TAC TTT GGG CTG CCA CGC TGG GTC ACC CTC CTG      798
Lys Trp Ser His Thr Tyr Phe Gly Leu Pro Arg Trp Val Thr Leu Leu
             40                  45                  50

CAG GAC TGG CAT GTC ATC CTG CCA CGT AAA CAC CAT CGC ATC CAC CAC      846
Gln Asp Trp His Val Ile Leu Pro Arg Lys His His Arg Ile His His
         55                  60                  65

GTC TCA CCC CAC GAG ACC TAC TTC TGC ATC ACC ACA GGC TGG CTC AAC      894
Val Ser Pro His Glu Thr Tyr Phe Cys Ile Thr Thr Gly Trp Leu Asn
 70              75                  80                  85

TAC CCT CTG GAG AAG ATA GGC TTC TGG CGA CGC CTG GAG GAC CTC ATC      942
Tyr Pro Leu Glu Lys Ile Gly Phe Trp Arg Arg Leu Glu Asp Leu Ile
             90                  95                  100

CAG GGC CTG ACG GGC GAG AAG CCT CGG GCA GAT GAC ATG AAA TGG GCC      990
Gln Gly Leu Thr Gly Glu Lys Pro Arg Ala Asp Asp Met Lys Trp Ala
             105                 110                 115

CAG AAG ATC AAA TAACTTCTCC GAGCCTGCTA CCTGGTTGCC AACCTTCCCT          1042
Gln Lys Ile Lys
         120

AGCCCCCAAA CCGAAGCCAT CTGCCAAATT CCAGCCTCTT TGAGCTGGCC CCTCCAGATG   1102

GAGAGGACAT CTCCTGGGCT GGGCCCAGGT ACCCCAGCCC ACCCCTCATG ACACAGAATA   1162

CTTGAGCCAC TGATTTTTCA TTTCTTTTTT TTTTTTTTCC TCGGCCCCTC CTCAGCCACC   1222

TGAGTTGCTC TATCTGCAAG CCTGACTCTG CCAGCCTCCC CTGGTAGAGA GGAGGTTTAC   1282

CCACTCCCTG CACGCCTGCC GTCCCTGCCC CGCTGGGCAG CCCTTCAGTG TGGCTGGCGT   1342

TGGGGCCAGT GAGTTGCCTC TTTCCCTCCT TGTCTGGCCC CAGTGGTCTG GGGAGCCCCC   1402

AGGCACACCT AAGCGTCGTG GAGCATTGTT CTGCCACAGC CCTGCATACT GACCCCGGGA   1462

GGCTGGGCAG GTGGACAGCC CCAGCCACCA CCTTCAGCCT AGCCTGTCCC CCAAGGATGG   1522

TGAAGCTCAG CAGGGGTCTG AGGGTAGCCG GCCAGAAGAG GCTGGAACCT CCTGCTCAAG   1582

TCTAGACCCC TACTTCTCTG CTGCCCCCAC CCTGCCAGAG CTGATGTTTC CAATACCAAG   1642

ATGTCTTCAC AGGGCACAGC CCCTGCAGAG CATCTTGGTC ATTTGGAAGA GGACACGGTA   1702

TCCCCTCTGG CCAGAGTATG TCAGAGAAGG AAGAGTAGGG CTTTTTTGTT TTGTTTTTTT   1762

TTAAAGGTGC TTGCTTGTTT AATGTAAATA ATAGAAAGCC TTAATATCTT TTCTGTAACA   1822

CGGAGTAATA TTTTAATGTC ATGTTTTGGA TGTACATAAT ATATTTATAA CAAAGAAAAA   1882

AAAAAAAAAA AAAAAAAAAA AAAAAA                                        1908
```

DNA AND PROTEIN FOR THE DIAGNOSIS AND TREATMENT OF ALZHEIMER'S DISEASE

This application is a continuation of PCT/JP96/03630 filed Dec. 12, 1996.

TECHNICAL FIELD

The present invention relates to DNAs each having a complementary sequence to the RNA strand of an mRNA expression level of which varies in the brain of a patient with Alzheimer's disease, compared with the mRNA expressed in the brain of normal human subjects, DNAs fragments hybridizable with such DNAs, polypeptides encoded by the DNAs and antibodies recognizing the polypeptides.

BACKGROUND ART

It is estimated that about 100,000 genes are present in human chromosomes. The expression of these genes is controlled by a good-balanced regulation mechanism for a long term, whereby human bodies can be maintained healthy. More specifically, quantitative and qualitative disorders of the expression of the genes including for example the abnormal expression of the genes or the expression of abnormal gene products due to mutation cause a variety of diseases. If an abnormally expressed gene specific to a disease is identified, the gene and the protein encoded by the gene can be used for the diagnosis and therapeutic treatment of the disease.

The research works on the analysis of human genes are very meaningful not only for satisfying the interest from the field of basic biology but also for the development and research works of medicinal products and diagnostic agents. From such respect, the human genome projects for the elucidation of the entire nucleotide sequences of human genome are now under way worldwide.

However, even the currently top level scientific technology requires a long period of time for the elucidation of the whole structure of human genome, and therefore, a cDNA project to elucidate only the expressed genetic information has been drawing attention.

So far reported research works include, for example, reports about the determination of the partial sequences of cDNAs randomly selected from a cDNA library from human brain [Science 252, 1651–1656 (1991); Nature 355, 632–634 (1992); Nature Genetics 2, 180–185 (1992); Nature Genetics 4, 256–267 (1993); Nature Genetics 4, 373–380 (1993)], a report about the determination of the partial sequences of cDNAs randomly selected from a cDNA library from a human liver cell line [Nature Genetics 2, 173–179 (1992)], a report about the determination of the partial sequences of cDNAs randomly selected from a cDNA library of human islets of Langerhans [Human Molecular Genetics 2, 1793–1798 (1993)] and a report about the determination of the partial sequences of cDNAs randomly selected from a human keratinocyte cDNA library [Biochem. Biophys. Res. Communi. 202, 976–983 (1994)], or a report about the determination of the nucleotide sequence of a cDNA randomly selected from a cDNA livrary derived from a human cultivated cell line (WO 94/03599).

Because these reports have been attained with major attention focused on the determination of the nucleotide sequences, where the structures of these randomly selected genes have been elucidated, the functions of the products of these genes have simply been anticipated on the basis of the examination of the homology between unknown genes and known genes or proteins already analyzed and registered in the data base, although the information of the structures of these genes have been brought about. Thus, these reports cannot directly provide information from the respect of such an application as the development of pharmaceutical products.

DISCLOSURE OF THE INVENTION

Focusing their attention to the fact that a gene expression level of which varies quantitatively or qualitatively in a patient with a disease has some function related to the pathological disorders, the present inventors have expected that simple and thorough screening of a cDNA which expression is abnormal in a patient with a disease to elucidate the structure thereof may serve well as a genetic analysis truly useful for the development and research works of the pharmaceutical products and the like of the disease. Therefore, the inventors have intensively progressed their works of the cDNA analysis. Consequently, the inventors have developed high-density cDNA filter analysis (referred to as "HDCFA" hereinafter) which enables the simple analysis of the expression levels of a vast amount of genes.

According to the method, mRNA with the increase or decrease in the expression level thereof in the brain of patients with Alzheimer's disease can be identified, compared with the expression level of the mRNA in normal human brain, and by recovering thereafter a DNA having a complementary sequence to the RNA strand of the mRNA, the present invention has been completed.

The present invention relates to DNAs each having a complementary sequence to the RNA strand of an mRNA expression of which is increased or decreased in the brain of patients with Alzheimer's disease, compared with the mRNA expressed in the brain of normal human subjects, DNAs hybridizable with such DNAs, polypeptides encoded by the DNAs, antibodies recognizing the polypeptides and the diagnosis, therapeutic treatment and research works of Alzheimer's patients using the DNAs, the polypeptides and the antibodies.

The present invention relates to DNAs complementary to the RNA strand of the mRNA, expression level of which varies in the brain of patients with Alzheimer's disease, compared with the mRNA expressed in the brain of normal human subjects, for example, a DNA having the nucleotide sequence selected from Sequence Nos. 1 to 17 and a DNA wherein one or more nucleotides in said DNA are deleted or substituted with other nucleotides or one or more nucleotides are added to said DNA, which is hybridizable with said DNA under stringent conditions. DNAs hybridizable under stringent conditions include a DNA with the nucleotide sequence 60% or more, preferably 80% or more and more preferably 95% or more homologous with the nucleotide sequence of a DNA having the nucleotide sequence selected from Sequence Nos.1 to 17.

Herein, each of the DNAs having one of the nucleotide sequences of Sequence Nos. 1 to 15 has a complementary sequence to the RNA strand of mRNA with the increase in the expression level in the brains of patients with Alzheimer's disease, and preferably, the increase in the expression level is 2-fold or more. Each of the DNAs having one of the nucleotide sequences of Sequence Nos.16 and 17 has a complementary sequence to the RNA strand of mRNA with the decrease in the expression level in the brain of patients with Alzheimer's disease, and preferably, the decrease in the expression level is 0.5-fold or less.

A DNA wherein one or more nucleotides in said DNA are deleted or substituted with other nucleotides or one or more nucleotides are added to said DNA can be generated by methods described in Nucleic Acids Research, 10, 6487 (1982), Proc. Natl. Acad. Sci., U.S.A., 79, 6409 (1982), Proc. Natl. Acad. Sci., U.S.A., 81, 5662(1984), Science, 224, 1431(1984), PCT WO 85/00817(1985), Nature, 316, 601 (1985), Gene, 34, 315 (1985), Nucleic Acids Research, 13, 4431(1985), Current Protocols in Molecular Biology, Chapter 8, Mutagenesis of Cloned DNA, John Wiley & Sons, Inc. (1985) and the like.

The term "DNA hybridizable under stringent conditions" means a DNA recovered by colony hybridization or plaque hybridization using as the probe a DNA complementary to the RNA strand of the mRNA with the expression level varied in the brain of Alzheimer's patients, compared with the expression level of the mRNA in normal human brain; more specifically, such DNA can be identified by the process comprising hybridizing in the presence of 0.7 to 1.0 M NaCl at 65° C. using a filter immobilized with the DNA derived from the colony or plaque and washing the filter using 0.1× to 2×SSC solutions (1×SSC solution is composed of 150 mM sodium chloride and 15 mM sodium citrate) under a condition of 65° C. The hybridization can be carried out according to the method described in Molecular Cloning, A Laboratory Manual, Second Edition, Sambrook, Fritsch & Maniatis, ed., Cold Spring Harbor Laboratory Press, 1989.

The polypeptides of the present invention are a polypeptides encoded by the DNAs, for example, a polypeptide encoded by a DNA having the nucleotide sequences selected from Sequence Nos. 1 to 17, or a polypeptide encoded by a DNA wherein one or more nucleotides in said DNA are deleted or substituted with other nucleotides or one or more nucleotides are added to said DNA, which is hybridizable with the DNA under stringent conditions.

The antibodies of the present invention include an antibody recognizing the polypeptide.

The DNAs of the present invention (referred to as "Alzheimer's disease-related DNA" hereinafter) are prepared by according to following steps;
1. preparing a human brain cDNA library;
2. preparing high-density cDNA filters using a cDNA derived from human brain;
3. preparing mRNAs from the brains of human patients with Alzheimer's disease and human subjects except Alzheimer's patients to prepare $^{32}$P-labeled cDNA probes;
4. hybridizing the cDNA with the $^{32}$P-labeled cDNA probes on the high-density human brain cDNA filters;
5. analyzing the results of the hybridization using an image analyzer and then determining the DNA sequence.

The polypeptides of the present invention (the polypeptide is referred to as "Alzheimer's disease-related polypeptide" hereinafter) are prepared by the following process;
1. digesting the Alzheimer's disease-related polypeptide-coding region of the Alzheimer's disease-related DNA fragment with restriction enzymes according to a routine method and then inserting the digested fragment into an expression vector;
2. introducing the expression vector in a host cell capable of expressing the objective Alzheimer's disease-related polypeptide according to a routine method to recover a transformant;
3. cultivating the transformant by a routine method to express and accumulate the objective Alzheimer's disease-related polypeptide;
4. purifying the accumulated Alzheimer's disease-related polypeptide by a routine method.

The antibodies of the present invention are prepared by the following process;

1. administering an antigen, namely a purified product of the Alzheimer's disease-related polypeptide of the whole length or a partial fragment thereof, subcutaneously, intravenously or peritoneally to rats, mice or hamsters aged 3 to 20 weeks, together with an appropriate adjuvant, for example complete Freund's adjuvant or aluminium hydroxide gel with *B. pertussis* vaccine to immunize the rats, mice or hamsters. The antigen should be administered five to 10 times every one to two weeks after the first administeration;
2. collecting serum from blood drawn from the ocular fundus plexus venosum on 3rd to 7th day after each administeration;
3. recognizing the reaction of the sera with the antigen by ELISA [see Enzyme-linked Immunoassay (ELISA), Igaku Shoin, 1976] and the like;
4. purifying the antibody from the sera, which was recognized to react with the antigen, according to the routine method.

The present invention is now described in detail hereinafter.

1. Preparation of DNAs
(1) Preparation of a human brain cDNA library

From normal human brain is extracted the total RNA by routine methods such as acid guanidine phenol chloroform method (Analytical Biochemistry, 162, 156–159, 1987), guanidine cesium chloride method, guanidium thiocyanate method [Methods in Enzymology, 164, Academic Press (1987), Okayama et al.] and the like.

By column method or batch method using oligo-dT cellulose, poly(A)$^+$ RNA is prepared from the RNA.

Using the poly(A)$^+$ RNA as the template, the cDNA is synthesized by using a reverse transcriptase according to a method such as Okayama-Burg method [Mol. Cell. Biol., 2, 161–170 (1982)] and Gubler-Hoffman method [Gene 25, 263–269 (1983)].

According to a routine method such as the method by Sambrook [EMBO. J., 4, 91–103 (1985)] and the method by Hyunh, T. V [DNA Cloning, A Practical Approach (D. M. Glover, ed.), 1, 49, IRL Press, Oxford], the cDNA is incorporated in a plasmid or a phage vector.

Any plasmid or phage vector autonomously replicable in a host cell to stably maintain the cDNA may be used to incorporate the cDNA therein. Specific examples thereof include plasmids of pBR322, pUC119, etc., phage vectors of λ gt10, λ ZAPII, etc., and the like.

When the cDNA is incorporated in the plasmids of pBR322, pUC119, and the like, the plasmids are introduced into an appropriate host cell such as *Escherichia coli* and a microorganism belong to the genus Bacillus by electroporation method or calcium chloride method to transform the host cell; when the cDNA is incorporated in a phage vector, the phage vector is transduced in cultivated host cells by in vitro packaging and the like, to prepare a cDNA library.

(2) Preparation of high-density human brain cDNA filters

Plasmid DNAs are prepared from the cDNA library prepared above in (1), which are then denatured in 0.2N NaOH. About 1 μg of the DNAs are dotted on filters, 8×12 cm in size (Hybond-N$^+$ nylon membrane filter, manufactured by Amersham), by using an automatic gridding robot Biomek-1000 (manufactured by Beckman). Then, pBluescript plasmid DNA and the DNA encoding glycerol triphosphate dehydrogenase (referred to as "G3PD-DNA" hereinafter) are alternately dotted, adjacent to each sample dot.

The pBluescript plasmid DNA is dotted for background correction, while G3PD-DNA is dotted for the determination of internal standard. By such arrangement of the dots, the assay error due to the positions of the cDNA dots on the filters and the difference in hybridization level between the filters can be made the minimum. By dotting at a density as high as possible on a single filter, the procedures described below can be simplified. More specifically, a method comprising 300 to 400 dots on a single filter is mentioned.

After subjecting the filters to a heating process at 80° C. for one hour, the filters are irradiated with ultraviolet ray (at $1.2 \times 10^4$ μJ/cm$^2$) from a FUNA-UV-LINKER manufactured by Funakoshi to prepare high-density cDNA filters.
(3) Preparation of mRNAs from the human brains of Alzheimer's patients and human subjects except Alzheimer's patients and preparation of $^{32}$P-labeled cDNA probes By the same procedures as described in the method described above in (1), the total RNAs are prepared from the human brain of patients with Alzheimer's disease and the human brain of human subjects except Alzheimer's patients. The RNAs are solubilized in diethyl pyrocarbonate-treated water to a final concentration of 2–20 μg/μl.

Using the RNAs as the template, $^{32}$P-labeled cDNA probes are prepared according to a routine method. As the routine method includes for example a method by means of a kit (First Strand Synthesis Kit, manufactured by Stratagene).
(4) Hybridization of the $^{32}$P-labeled cDNA probes with the cDNA on the high-density cDNA filters The high-density human brain cDNA filters, which are prepared according to the method described above in (2), are immersed in a hybridization solution with addition of the DNA from salmon sperm [6×SSC solution (1×SSC solution is composed of 150 mM sodium chloride and 15 mM sodium citrate), 10×Denhardt's solution (1×Denhardt's solution is composed of 0.02% polyvinyl pyrrolidone, 0.02% bovine serum albumin, and 0.02% Ficoll), 1% SDS and 100 μg/ml DNA from salmon sperm], for pre-hybridization treatment at 65° C. After the pre-hybridization treatment, the $^{32}$P-labeled cDNA probe is added to the resulting mixture, for hybridization treatment overnight at 65° C. After the treatment, the filters are immersed in a solution containing 2×SSC and 1% SDS for heating at 65° C. for 15 minutes. After heating, the filters are immersed in a solution containing 0.1×SSC and 0.1% SDS for washing treatment at 65° C. for 15 minutes and subsequent drying in air.
(5) Quantitative analysis of the results of the hybridization using an image analyzer and determination of the DNA sequence The filters prepared according to the method described above in (4) are exposed to imaging plates for a Fuji bio-imaging analyzer of Model BAS 2000 System, to determine the radioactivity of each dot on the filters, by means of the Fuji bio-imaging analyzer of Model BAS 2000 System. The radioactivity of each dot is converted into relative luminous intensity score (referred to as "PSL") by using Auto Quant Quantitative Program. By subtracting from the PSL value of each cDNA clone thus recovered, the PSL value of the adjacent dot corresponding to the pBluescript plasmid DNA and subsequently normalizing the resulting PSL value using the PSL value of the internal standard G3PD-DNA positioned adjacently (reducing the experimental inter-filter and intra-filter errors due to the dot position), a data base is prepared.

Using the data base, the expression intensity of the probe from Alzheimer's patients is divided by the expression intensity of the probe from normal human subjects per each dot, to detect any probe with the variation of the expression intensity in the brain of Alzheimer's patients, compared with normal human brain.

In addition to such analysis method, the analysis method of the results of the hybridization includes any method capable of quantitatively analyzing the level of hybrids formed.

Among the plasmid DNAs from the human brain cDNA library dotted on the filters in the procedure (2), the DNA hybridized with the probe with the variation of the expression intensity in the brain of Alzheimer's patients compared with normal human brain can be identified.

The plasmid DNA contains a DNA with a complementary sequence to the RNA strand of the mRNA with the varied expression level in the brain of Alzheimer's patients, compared with normal brain.

The nucleotide sequence of the DNA in the plasmid DNA, having a complementary nucleotide sequence to the RNA strand of the mRNA with the varied expression level in the brain of Alzheimer's patients, compared with normal brain, can be determined by routine nucleotide sequencing methods, for example the dideoxy method by Sanger, et al. [Proc. Natl. Acad. Sci., U.S.A., 74, 5463, 1977]. Sequencing of nucleotide is carried out by using a nucleotide autosequencer, for example ABI 373 DNA Sequencer or 373A DNA Sequencer, manufactured by Applied Biosystems.

Specific examples of the nucleotide sequence of the DNA with a complementary nucleotide sequence to the RNA strand of the mRNA with the increase in the expression level in the brains of patients with Alzheimer's disease include the nucleotide sequences of Sequence Nos. 1 to 15, while specific examples of the nucleotide sequence of the DNA with a complementary nucleotide sequence to the RNA strand of the mRNA with the decrease in the expression level include the nucleotide sequences of Sequence Nos. 16 and 17.

*Escherichia coli* DH5 α/pGCS55 containing the plasmid DNA with the sequence of Sequence No. 1, *Escherichia coli* DH5 α/pGCS99 containing the plasmid DNA with the sequence of Sequence No.2, *Escherichia coli* DH5 α/pGCS198 containing the plasmid DNA with the sequence of Sequence No.3, *Escherichia coli* DH5 α/pGCS328 containing the plasmid DNA with the sequence of Sequence No.4, *Escherichia coli* DH5 α/pGCS335 containing the plasmid DNA with the sequence of Sequence No.5, *Escherichia coli* DH5 α/pGCS547 containing the plasmid DNA with the sequence of Sequence No.6, *Escherichia coli* DH5 α/pGCS998 containing the plasmid DNA with the sequence of Sequence No.7, *Escherichia coli* DH5 α/pGCS1148 containing the plasmid DNA with the sequence of Sequence No.8, *Escherichia coli* DH5 α/pGCS1180 containing the plasmid DNA with the sequence of Sequence No.9, *Escherichia coli* DH5 α/pGCS1243 containing the plasmid DNA with the sequence of Sequence No.10, *Escherichia coli* DH5 α/pGCS2232 containing the plasmid DNA with the sequence of Sequence No.11, *Escherichia coli* DH5 α/pGCS3282 containing the plasmid DNA with the sequence of Sequence No.12, *Escherichia coli* DH5 α/pGCS11037 containing the plasmid DNA with the sequence of Sequence No.13, *Escherichia coli* DH5 α/pGCS1984 containing the plasmid DNA with the sequence of Sequence No.16 and *Escherichia coli* DH5 α/pGCS2593 containing the plasmid DNA with the sequence of Sequence No.17, have been deposited with the National Institute of Bioscience and Human-Technology of the Agency of Industrial Science and Technology at 1-3, Higashi 1-chome, Tsukuba-shi, Ibaraki-ken, 〒305, Japan under FERM BP-5304 through 5316, 5318 and 5319, respectively, on the date of Nov. 28, 1995, in terms of the Budapest Treaty.

2. Preparation of a Alzheimer's disease-related polypeptide

So as to express the Alzheimer's disease-related DNA thus recovered above in a host cell, a DNA fragment containing the Alzheimer's disease-related DNA is digested with restriction enzymes or DNases into a DNA fragment of an appropriate length, containing the DNA encoding the Alzheimer's disease-related polypeptide (referred to as "Alzheimer's disease-related gene" hereinafter), which is then inserted in the downstream of a promoter in an expression vector. Subsequently, the expression vector inserted with the DNA is introduced in a host cell appropriate for the expression vector. As such host cell, use is made of any host cell capable of expressing the objective gene can be used. As examples of the host cell, prokaryotes belonging to the Escherichia, Serratia, Corynebacterium, Brevibacterium, Pseudomonas, Bacillus or the like, and yeast strains belong to the geuns Kluyveromyces, Saccharomyces, Schizosaccharomyces, Trichosporon, Schwanniomyces or the like; animal cell hosts and insect cell hosts and the like can be mentioned.

Any expression vector, which can be autonomously replicable in the above-mentioned host cell or is capable of being incorporated into a chromosome and which contains a promoter at a position where the Alzheimer's disease-related gene can be transcribed, can be used.

When a prokaryotic organism such as bacteria is used as such host cell, preferably, the expression vector for the Alzheimer's disease-related gene should be autonomously replicable in the prokaryotic organism and be composed of a promoter, a ribosome binding sequence, the Alzheimer's disease-related gene, and a transcription termination sequence. A regulatory gene of the promoter may be contained therein.

As example of the expression vector, mentioned are pBTrp2, pBTac1, pBTac2 (all are commercially available from Boehringer Mannheim), pKYP10 (Japanese Published Unexamined Patent Application No. 110600/83), pKYP200 [Agric. Biol. Chem., 48, 669(1984)], pLSA1 [Agric. Biol. Chem., 53, 277(1989)], pGEL1 [Proc. Natl. Acad. Sci., U.S.A., 82, 4306 (1985)], pBluescript (Stratagene), pTrs30 [prepared from *Escherichia coli* JM109/pTrS30 (FERM BP-5407)] and pTrs32 [prepared from *Escherichia coli* JM109/pTrS32 (FERM BP-5408)].

As the promoter, usable is any promoter capable of being expressed in a host cell such as *Escherichia coli*. For example, mentioned are promoters derived from *Escherichia coli*, phages, etc., such as trp promoter (Ptrp), lac promoter (Plac), $P_L$ promoter, and $P_R$ promoter. Also, usable are artificially designed and modified promoter, such as a promoter (Ptrp×2) composed of two Ptrp's in tandem series, tac promoter and the like.

As ribosome binding sequence, any ribosome binding sequence capable of being expressed in a host cell such as *Escherichia coli* is used. Preferably, a plasmid with an appropriate distance (for example 6 to 18 nucleotides) between the ribosome binding sequence and the initiation codon may be used.

The transcription termination sequence is not always necessary required for the expression of the gene, but, it is desirable that a transcription termination sequence is arranged immediately downstream the structural gene.

As the host cell, *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Bacillus subtilis*, *Bacillus amyloliquefacines*, *Brevibacterium immariophilum* ATCC14068, *Brevibacterium saccharolyticum* ATCC14066, *Brevibacterium flavum* ATCC14067, *Brevibacterium lactofermentum* ATCC 13869, *Corynebacterium glutamicum* ATCC13032, *Corynebacterium acetoacidophilum* ATCC 13870, *Microbacterium ammoniaphium* ATCC15354 and the like can be mentioned.

When a yeast strain is used as a host cell, for example, YEp13 (ATCC37115), YEp24 (ATCC37051), YCp50 (ATCC37419), and the like can be used as the expression vector.

As the promoter, any promoter capable of being active in a yeast bacterial strain may be used. AS examples of promoters, promoters of glycolytic genes such as hexose kinase, gal 1 promoter, gal 10 promoter, heat shock protein promoter, MF α1 promoter, CUP 1 promoter and the like can be used.

As examples of the host cell, *Saccharomyces cerevisae*, *Schizosaccharomyces pombe*, *Kluyveromyces lactis*, *Trichosporon pullulans*, *Schwanniomyces alluvius* and the like can be mentioned.

When an animal cell is used as the host cell, for example, pcDNAI/Amp, pcDNAI, pcDM8 (all commercially available from Funakoshi), pAGE107 [Cytotechnology, 3, 133 (1990)], pAGE103 [Journal of Biochemistry, 101, 1307 (1987)] and the like can be used as the expression vector.

As the promoter, any promoter capable of being active in animal cells may be used, For example, the promoter for the IE (immediate early) gene of human CMV and the like can be used. Additionally, the enhancer for the IE gene of human CMV may be used together with the promoter.

As examples of the host cell, Namalwa cell, HBT5637 (Japanese Published Unexamined Patent Application No. 299/88), COS cell, CHO cell and the like can be used.

As the method for introducing the DNA into animal cells, any and ever method capable of introducing DNA into animal cells may be used. For example, employable are electroporation method [Miyaji et al., Cytotechnology, 3, 133(1990)], calcium phosphate method (Japanese Published Unexamined Patent Application No. 227075/90), lipofection method [Philip L. Felgner, et al., Proc. Natl. Acad. Sci., U.S.A., 84, 7413(1987)] and the like. The resulting transformants can be obtained and cultivated according to the method described in Japanese Published Unexamined Patent Application No. 227075/90 or 257891/90.

For insect cells, insect cells such as Sf9 and Sf21 (all manufactured by Farmingen), which are infected with the recombinant Baculovirus [Bio/Technology, 6, 47(1988)] prepared by using the BaculoGold Starter Kit manufactured by Farmingen, can be used.

By cultivating a transformant carrying the recombinant DNA comprising the Alzheimer's disease-related gene, according to a routine cultivation method, to generate and accumulate the Alzheimer's disease-related polypeptide and recovering the Alzheimer's disease-related polypeptide from the culture, the Alzheimer's disease-related polypeptide can be produced.

When the transformant for producing the Alzheimer's disease-related polypeptide is a prokaryote such as *Escherichia coli* or an eucaryote such as yeast, the medium for cultivating these organisms may be any medium, natural or synthetic, as long as the medium contains a carbon source, a nitrogen source, inorganic salts and the like, all of which the organisms can assimilate to effectively cultivate the transformant.

Any carbon source which the individual microorganisms can assimilate may be used satisfactorily, such as carbohydrates such as glucose, fructose, sucrose, molasses containing these carbon sources, starch and starch hydrolysate; organic acids such as acetic acid and propionic acid; and alcohols such as ethanol and propanol.

As the nitrogen source, ammonia; ammonium salts of various inorganic acids and organic acids, such as ammonium chloride, ammonium sulfate, ammonium acetate, and ammonium phosphate; other nitrogen-containing compounds; peptone, meat extract, yeast extract, corn steep liquor, casein hydrolysate, soy bean bran and soy bean bran hydrolysate, various cultivated cells, digested products thereof and the like may be used.

As inorganic substances, potassium dihydrogen phosphate, dipotassium hydrogen phosphate, magnesium phosphate, magnesium sulfate, sodium chloride, ferrous sulfate, manganese sulfate, copper sulfate, calcium carbonate and the like may be used.

For cultivation of fungi, cultivation medium, containing a carbonsource such as wheat bran, rice bran, or the like, a nitrogen source and an inorganic source and being supplemented with appropriate salts, may be used.

Cultivation is carried out under aerobic conditions such as shaking culture or submerged-aerial stirring culture. The cultivation temperature is preferably 15 to 40° C. and the cultivation period is generally 16 to 96 hours. The pH should be maintained at 3.0 to 9.0 during the cultivation. The pH is adjusted by using inorganic or organic acids, alkali solutions, urea, calcium carbonate, ammonia and the like.

During cultivation, an antibiotic such as ampicillin and tetracycline may satisfactorily be added to a cultivation medium, if necessary.

For cultivating a microorganism transformed with an expression vector using an inducible promoter as the promoter, an inducer is satisfactorily added to the cultivation medium if necessary. For cultivating a microorganism transformed with an expression vector using lac promoter, for example, isopropyl-β-D-thiogalactopyranoside (IPTG) is added to the cultivation medium; for cultivating a microorganism transformed with an expression vector using trp promoter, indole acrylic acid (IAA) is satisfactorily added to the cultivation medium.

When the transformant for producing the Alzheimer's disease-related polypeptide is an animal cell, RPMI 1640 medium and Eagle's MEM medium which are general used or these media containing a fetal bovine serum or the like can be used, as the medium for cultivating the cell.

Cultivation is carried out under conditions in the presence of 5% $CO_2$. The cultivation temperature is preferably 35 to 37° C., and the cultivation period is generally 3 to 7 days.

During cultivation, if necessary, an antibiotic such as kanamycin and penicillin is added to the cultivation medium.

So as to isolate and purify the Alzheimer's disease-related polypeptide from the culture of the transformant for producing the Alzheimer's disease-related polypeptide, general methods for isolating and purifying enzymes may be used.

When the Alzheimer's disease-related polypeptide is accumulated in the cells of the transformant for producing the Alzheimer's disease-related polypeptide, the culture is centrifuged to collect the cells in the culture, and the cells are washed and then disrupted by means of an ultrasonicator, a French press, a Manton-Gaulin homogenizer, a dinomill and the like, whereby a cell-free extract can be recovered. From the supernatant of the centrifuged cell-free extract, thereafter, a purified product can be recovered by salting out with ammonium sulfate or the like, desalting, precipitation by an organic solvent, anion exchange chromatography using resins such as diethylaminoethyl (DEAE)-Sepharose and DIAION HPA-75 (manufactured by Mitsubishi Chemical), cation exchange chromatography using resins such as S-Sepharose FF (manufactured by Pharmacia), hydrophobic chromatography using resins such as butyl Sepharose and phenyl Sepharose, gel filtration using molecular sieve, chromato-focusing and electrophoresis such as isoelectric focusing.

When the Alzheimer's disease-related polypeptide is secreted outside cells, the culture is treated with a procedure such as centrifugation, to recover a soluble fraction. From the soluble fraction, the purified product of the Alzheimer's disease-related polypeptide can be recovered by the same method as the above-mentioned method for isolation and purification from the supernatant of the cell-free extract.

3. Preparation of Alzheimer's disease-related antibody

The a purified product of whole length or a partial fragment of the Alzheimer's disease-related polypeptide (antigen), as recovered above in 2. Is administered at about 50 to 100 μg/animal, subcutaneously, intravenously or peritoneally, to rats, mice or hamsters aged 3 to 20 weeks, together with an appropriate adjuvant, for example complete Freund's adjuvant or aluminium hydroxide gel with *B. pertussis* vaccine.

The antigen need be administered five to 10 times every one to two weeks after the first administration. After each administration, serum is collected from blood drawn from the ocular fundus plexus venosum on the 3ed to 7th day. The reaction of the sera with the antigen is recognized by ELISA [see Enzyme-linked Immunoassay (ELISA), Igaku Shoin, 1976; Antibodies—A Laboratory Manual, Cold Spring Harbor Laboratory, 1988] and the like.

From the mice, rats or hamsters of which the sera have sufficient antibody titers to the antigen used for their immunization, the sera are collected to recover a purified antibody from the sera by using routine methods such as salting out by means of 40 to 50% saturated ammonium sulfate, caprylic acid precipitation, chromatography methods using for example DEAE-Sepharose column, protein A column or gel filtration column.

4. Diagnosis and therapeutic treatment of patients with Alzheimer's disease (1) Using as a diagnostic agent the DNA which is identified according to the method described in 1.–(5) and has a complementary nucleotide sequence to the RNA strand of the mRNA with the increase in the expression level in the brains of patients with Alzheimer's disease (referred to as "diagnostic DNA" hereinafter), patients with Alzheimer's disease can be identified.

According to the method described in 1.–(2), more specifically, the diagnostic DNA is dotted on filters to prepare DNA filters. According to the method described in 1.–(3), $^{32}$P-labeled cDNA probes are individually prepared from the brains of a test patient and normal subjects. The $^{32}$P-labeled cDNA probes are used for hybridization with the diagnostic DNA on the DNA filters according to the method described in 1.–(4), to compare the expression level of the gene corresponding to the hybridizing probes between the test patients and normal subjects according to the method described in 1.–(5). Definite diagnosis of as to whether or not the test patient is afflicted with Alzheimer's disease depends on whether or not the pattern of the expression level of the gene corresponding to the diagnostic DNA in the test patient agrees with the pattern of the expression of the gene in patients with Alzheimer's disease.

(2) Using the antibody recovered by the method described in 3., the amount of the Alzheimer's disease-related polypeptide in the tissue extract of the test patient is assayed by radioimmunoassay after labeling the Alzheimer's disease-related polypeptide with a radioisotope.

Whether or not the test patient afflicted with Alzheimer's disease can be diagnosed, depending on, according to the determination method as mentioned above, whether or not the amount of the Alzheimer's disease-related polypeptide matches with the pattern of Alzheimer's patients.

(3) The polypeptide encoded by the DNA which expression level is decreased in patients with Alzheimer's disease can be used as a therapeutic agent for treating Alzheimer's patients for a therapeutic method comprising supplementing the patients with the polypeptide, while the polypeptide encoded by the DNA which expression level is increased in patients with Alzheimer's disease is useful for the preparation of an antibody recognizing the polypeptide. Therefore, the antibody can be used as a therapeutic agent for treating Alzheimer's patients for a therapeutic method comprising suppressing the action of the polypeptide.

(4) The DNAs of the present invention can be used as a gene for gene therapy of Alzheimer's disease, while the antisense nucleic acid corresponding to the present cDNA can be used as a nucleic acid for gene therapy of Alzheimer's disease.

(5) The DNAs, polypeptides and antibodies of the present invention can be used as a reagent for research works regarding the mechanism of the onset of Alzheimer's disease.

BEST MODES OF CARRYING OUT THE INVENTION

The present invention is now described with reference to the following examples.

EXAMPLE 1

(1) Preparation of a human brain cDNA library

From the normal region of the frontal cortex of a Japanese male patient (aged 59 years) with glioblastoma, the total RNA was extracted by acid guanidine phenol chloroform method (Analytical Biochemistry, 162, 156–159, 1987). Poly A$^+$ RNA was purified from the total RNA by using a commercially available "oligo-dT". Using the polyA$^+$ RNA of 5 $\mu$g as the template, together with a reverse transcriptase Superscript™ and Ribonuclease H manufactured by BRL and *Escherichia coli* DNA polymerase I and T4 DNA polymerase manufactured by Takara Shuzo, a cDNA library ($\lambda$ phage) was prepared by means of a $\lambda$ ZAP II vector kit manufactured by Stratagene. The thus recovered phage particles of 1×10$^5$ or more were mixed with 200 $\mu$l of a culture of *Escherichia coli* XL1-Blue (OD$_{600}$=1) and 1 $\mu$l of helper phage R408, for cultivation at 37° C. for 15 minutes, followed by addition of 2×YT cultivation medium (5 ml) (16 g/l Bacto-tryptone, 10 g/l yeast extract, 5 g/l NaCl, pH 7.0) for cultivation at 37° C. for 3 hours. After cultivation, the resulting culture was heated at 70° C. for 20 minutes and centrifuged at 4000×g for 5 minutes, to recover a supernatant containing the recombinant phagemid.

The phagemid solution (200 $\mu$l) was mixed with an equal volume of the *Escherichia coli* XL1-Blue culture, for cultivation at 37° C. for 15 minutes, and a part of the mixture was then spread on a petri dish containing a 50 $\mu$g/ml ampicillin-containing LB medium (10 g/l Bacto-peptone, 5 g/l yeast extract, 10 g/l NaCl, pH 7.0) to a final occurrence of several hundreds of colonies, and followed by cultivation at 37° C. overnight. Each of the colonies appearing on the next morning was independently cultivated in a 50 $\mu$g/ml ampicillin-containing 2×YT cultivation medium (5 ml) at 37° C. for 12 hours. From the cultivated cells recovered from the culture, plasmid DNA was purified by using an automatic extraction system PI-100 manufactured by Kurabo.

Digesting 100 plasmid DNAs with restriction enzymes EcoRI and XhoI for analysis by agarose gel electrophoresis, almost all the plasmids contained inserts of 0.4 kb or more. By subsequently using Taq Dye Primer™ Cycle Sequencing Kit (Applied Biosystems), cycle sequencing was started from the 3' terminus of the cDNA, to determine a partial nucleotide sequence by ABI 373 DNA sequencer (Perkin Elmer). The homology of the resulting DNA sequences was examined on the basis of the GenBank DNA data base. Consequently, it was demonstrated that the sequences of the genes relating to mitochondria occupied about 30% while about 70% of the remaining sequences were novel genes.

(2) Preparation of high-density cDNA filters

By the method described in Example 1, from the human cerebral cortex cDNA library, 15,256 plasmid DNAs were independently extracted. From the cDNA library, clones containing the mitochondria-related genes were removed. About 1 $\mu$g of the plasmid DNAs from 8353 clones were denatured with 0.2 N NaOH, which were then dotted on a Hybond-N$^+$ nylon membrane filters (Amersham), 8×12 cm in size, by using an automatic gridding robot Biomek-1000 manufactured by Beckman. Furthermore, pBluescript vector DNA and G3PD-DNA were alternately dotted, adjacent to each sample dot.

The filters were treated under heating at 80° C. for one hour, followed by ultraviolet irradiation (at 1.2×10$^4$ $\mu$J/cm$^2$) from FUNA-UV-LINKER manufactured by Funakoshi to prepare high-density cDNA filters.

(3) Preparation of $^{32}$P-labeled cDNA probe

Using ISOGEN manufactured by Nippon Gene, cell-free extracts were prepared individually from the brains (each about 1 g) of patients with Alzheimer's disease and normal subjects, by means of a homogenizer of POLYTORON PT10 20 3500, to prepare individually the total RNAs according to the method instructed in the ISOGEN. To a final concentration of 10 $\mu$g/2.3 $\mu$l, each of the total RNAs was solubilized in diethyl pyrocarbonate-treated water.

Using 10 $\mu$g of each of the total RNAs thus recovered as a template, $^{32}$P-labelled cDNA probe was prepared as follows, using a kit manufactured by Stratagene (First Strand Synthesis Kit).

25 $\mu$l of $\alpha$-$^{32}$P-dCTP (6000 Ci/mmol; manufactured by New England and Nuclear) and 1 $\mu$l each of 1 mM dATP, dTTP, and dGTP were mixed with 0.2 $\mu$l of 0.5 $\mu$g/$\mu$l Oligo dT, and the resulting mixture was subsequently dried up by using a vacuum pump. The dried product was solubilized in 2.3 $\mu$l of the above mentioned RNA solution (10 $\mu$g/2.3 $\mu$) from human brain recovered, followed by addition of 0.8 $\mu$l of a 5×buffer solution and subsequent thorough mixing. The mixture solution was heated at 70° C. for 10 minutes, and was then immersed in ice for rapid cooling.

To the solution was added 4 $\mu$l of 0.1M DTT for heating at 42° C. for 2 minutes, followed by addition of 0.5 $\mu$l of Super Script II, and then a reaction was carried out at 42° C. for 30 minutes. To the resulting reaction solution were added 0.4 $\mu$l of 25 mM dNTP, 1 $\mu$l of 5×buffer solution, 0.5 $\mu$l of 0.1M DTT, 2.6 $\mu$l of diethyl pyrocarbonate-treated water, and 0.5 $\mu$l of Super Script II, for reaction at 42° C. for 30 minutes. To the resulting reaction solution was added 3 $\mu$l of 0.5M EDTA, followed by subsequent addition of 10 $\mu$l of TE (10 mM Tris-HCl, pH 7.0, 1 mM EDTA), to remove free $^{32}$P-dCTP by spin column method using Quick Spin™ Columns Sephadex G50, fine, manufactured by Boehringer Mannheim.

(4) Hybridization of the $^{32}$P-labeled cDNA probe with the cDNAs on the high-density cDNA filters The high-density cDNA filters prepared in Example 1 (2) were immersed in a hybridization solution with addition of the DNA derived from salmon sperm, for pre-hybridization treatment at 65° C. The $^{32}$P-labeled human brain cDNA prepared in Example 1 (3) was added to the resulting treated solution, and the following hybridization treatment was carried out.

A distilled water was added to the $^{32}$P-labeled human brain cDNA prepared in Example 1 (3) to a final volume of 500 μl, followed by addition of 17 μl of 10N NaOH for denaturing of the cDNA. After adding 17 μl of 10N HCl to the resulting mixture for neutralization of the mixture, the mixture was added to the solution treated for pre-hybridization, and hybridization treatment was conducted overnight at 65° C. The filters thus treated were washed in a solution containing 2×SSC and 1% SDS at 65° C. for 15 minutes and in a solution containing 0.1×SSC and 1% SDS at 65° C. for 15 minutes, followed by drying in air.

(5) Quantitative analysis of the hybridization results using an image analyzer

The filters prepared in Example 1 (4) were exposed to an imaging plates for Fuji bio-imaging analyzer BAS2000 System for 5 to 10 hours, and then, the radioactivity from each dot on the filters was determined by using the Fuji bio-imaging analyzer BAS 2000 System.

The radioactivity of each dot was converted into relative luminous intensity score (referred to as "PSL") by using the Auto Quant Quantitative Program. By subtracting, from the PSL value of the plasmid DNA derived from each cDNA clone thus recovered, the PSL value of the adjacent dot corresponding to the pBluescript plasmid DNA and subsequently normalizing the resulting PSL value using the PSL value of the internal standard G3PD-DNA positioned adjacently, a data base was prepared.

By dividing the expression intensity of the probe from Alzheimer's patients by the expression intensity of the probe from normal human subjects per each dot using the data base, detecting a probe with the modification in the expression intensity in the brain of Alzheimer's patients, compared with the brain of normal human subjects, a plasmid DNA hybridized with the detected probe was identified from the human brain cDNA library used for dotting in Example 1 (2).

The plasmid DNA contains a DNA with a complementary sequence to the RNA strand of the mRNA with the varied expression level in the brain of Alzheimer's patients, compared with normal brain.

Among the plasmid DNAs, 15 types of plasmid DNAs individually containing a DNA with a complementary nucleotide sequence to the RNA strand of the mRNA with the increase in the expression level by two-fold or more in the brain of Alzheimer's patients, and 2 types of plasmid DNAs individually containing such DNA with the decrease in the expression level of the mRNA by 0.5-fold or less were identified.

The results are shown in Table 1.

TABLE 1

| | Expression level in Alzheimer's patients, compared with normal subjects | |
|---|---|---|
| Plasmid | Sequence No. | Ratio of expression levels (patients/normal subjects) |
| pGCS55 | 1 | 10.7 |
| pGCS99 | 2 | 4.7 |
| pGCS198 | 3 | 11.5 |
| pGCS328 | 4 | 10.6 |
| pGCS335 | 5 | 14.9 |
| pGCS547 | 6 | 15.2 |
| pGCS998 | 7 | 22.7 |
| pGCS1148 | 8 | 37.7 |
| pGCS1180 | 9 | 10.8 |
| pGCS1243 | 10 | 22.1 |
| pGCS2232 | 11 | 7.2 |
| pGCS3282 | 12 | 20.3 |
| pGCS11037 | 13 | 27.7 |
| pGCS427 | 14 | 14.5 |
| pGCS981 | 15 | 17.5 |
| pGCS1984 | 16 | 0.14 |
| pGCS2593 | 17 | 0.067 |

The DNA sequences with a complementary nucleotide sequence to the RNA strand of the mRNA with the increase in the expression level in the brain of Alzheimer's patients, which are contained in plasmid DNAs, pGCS55, pGCS99, pGCS198, pGCS328, pGCS335, pGCS547, pGCS998, pGCS1148, pGCS1180, pGCS1243, pGCS2232, pGCS3282, pGCS11037, pGCS427 and pGCS981 respectively, are shown as Sequence Nos.1to 15. The DNA sequences with a complementary nucleotide sequence to the RNA strand of the mRNA with the decrease in the expression level in the brain of Alzheimer's patients, which are contained in plasmid DNAs, pGCS1984 and pGCS2593 respectively, are shown as Sequence Nos.16 and 17. The DNA sequences were determined by the method by Sanger, et al.

EXAMPLE 2

Diagnosis of Alzheimer's patients

Using 17 types of diagnostic DNAs as specified in Example 1 (5), specifically the plasmid DNAs, namely pGCS55, pGCS99, pGCS198, pGCS328, pGCS335, pGCS547, pGCS998, pGCS1148, pGCS1180, pGCS1243, pGCS2232, pGCS3282, pGCS11037, pGCS427 and pGCS981, each containing a DNA with a complementary nucleotide sequence to the RNA strand of the mRNA with the increase in the expression level in the brain of Alzheimer's patients, as shown as Sequence Nos.1, 2, 3, 4, 5, 6, 7, 8, 9, 10, 11, 12, 13, 14 and 15, respectively and the plasmid DNAs, namely pGCS1984 and pGCS2593, each containing a DNA with a complementary nucleotide sequence to the RNA strand of the mRNA with the decrease in the expression level in the brain of Alzheimer's patients, as shown as Sequence Nos.16 and 17 respectively, diagnosis of Alzheimer's disease was made.

According to the method described in Example (2), the diagnostic DNAs were dotted on the filters, to prepare DNA filters. According to the method described in Example 1 (3), the brains of three Alzheimer patients and two normal subjects were used to prepare individual $^{32}$P-labeled cDNA probes.

The $^{32}$P-labeled cDNA probes were used for hybridization with the diagnostic DNAs on the DNA filters according to the method described in Example 1(4), and according to the method described in Example 1(5), and then the expression level of each of the genes individually corresponding to the hybridizing prove was compared between Alzheimer patients and normal subjects.

The results are shown in Table 2.

TABLE 2

Ratio of expression levels in Alzheimer patients compared with normal subjects

| Sequence No. | Ratio of expression levels (patients/normal subjects) | | |
|---|---|---|---|
| | Patient 1 | Patient 2 | Patient 3 |
| 1 | 5.2 | 4.5 | 5.9 |
| 2 | 2.0 | 2.6 | 2.5 |
| 3 | 2.9 | 5.2 | 3.4 |
| 4 | 6.3 | 5.5 | 6.6 |
| 5 | 2.4 | 2.8 | 6.4 |
| 6 | 5.4 | 5.7 | 4.8 |
| 7 | 6.0 | 10.3 | 16.5 |
| 8 | 7.7 | 9.2 | 14.1 |
| 9 | 8.3 | 6.5 | 10.2 |
| 10 | 3.3 | 8.3 | 18.3 |
| 11 | 4.9 | 4.7 | 7.7 |
| 12 | 6.0 | 7.4 | 15.3 |
| 13 | 3.2 | 7.3 | 23.8 |
| 14 | 2.4 | 3.9 | 8.2 |
| 15 | 3.3 | 6.4 | 12.3 |
| 16 | 0.14 | 0.25 | 0.35 |
| 17 | 0.25 | 0.38 | 0.25 |

As shown in Table 2, the expression levels of the genes corresponding to the Sequence Nos.1 to 17 in the Alzheimer patients are so varied to be discriminated from the levels thereof in normal subjects. It is indicated that the method is useful for diagnosing Alzheimer's disease.

Industrial Applicability

The DNAs of the present invention can be used for the diagnosis, therapeutic treatment and research works of patients with Alzheimer's disease and for the production of the polypeptides encoded by the DNAs. The polypeptides of the present invention can be used for the diagnosis, therapeutic treatment and research works of patients with Alzheimer's disease and for the production of an antibodies recognizing the polypeptides. The antibodies of the present invention can be used for the diagnosis and therapeutic treatment of patients with Alzheimer's disease and as a research source of patients with Alzheimer's disease.

We claim:

1. A DNA comprising a nucleotide sequence selected from the group consisting of SEQ ID NOS: 1, 2, 3, 4, 5, 6, 7, 8, 9, 10, 11, 12, 13, 14, 15, 16 and 17.

2. An isolated DNA sequence selected from the group consisting of SEQ ID NOS: 1, 2, 3, 4, 5, 6, 7, 8, 9, 10, 11, 12, 13, 14, 15, 16 and 17, wherein one or more nucleotides are deleted, added or substituted with other nucleotides and wherein said DNA hybridizes specifically with a DNA comprising a nucleotide sequence selected from the group consisting of SEQ ID NOS: 1, 2, 3, 4, 5, 6, 7, 8, 9, 10, 11, 12, 13, 14, 15, 16 and 17 under stringent conditions.

3. A diagnostic agent of patients with Alzheimer's disease, containing a DNA comprising a nucleotide sequence selected from the group consisting of SEQ ID NOS: 1, 2, 3, 4, 5, 6, 7, 8, 9, 10, 11, 12, 13, 14, 15, 16 and 17.

* * * * *

UNITED STATES PATENT AND TRADEMARK OFFICE
CERTIFICATE OF CORRECTION

PATENT NO.   : 5,936,078
DATED        : August 10, 1999
INVENTOR(S)  : TETSURO KUGA ET AL.

It is certified that error appears in the above-identified patent and that said Letters Patent is hereby corrected as shown below:

COLUMN 1:

Line 59, "livrary" should read --library--.

COLUMN 8:

Line 13, "AS examples" should read --As examples--;
    Line 28, "used, For" should read --used. For--; and
    Line 36, "ever" should read --every--.

COLUMN 10:

Line 17, "The a purified" should read
            --The purified--; and
    Line 28, "3ed" should read --3rd--.

UNITED STATES PATENT AND TRADEMARK OFFICE
CERTIFICATE OF CORRECTION

PATENT NO. : 5,936,078
DATED : August 10, 1999
INVENTOR(S) : TETSURO KUGA ET AL.

It is certified that error appears in the above-identified patent and that said Letters Patent is hereby corrected as shown below:

COLUMN 14:

Line 31, "Nos.1to 15" should read --Nos. 1 to 15--.

Signed and Sealed this

Third Day of April, 2001

Attest:

NICHOLAS P. GODICI

Attesting Officer

Acting Director of the United States Patent and Trademark Office